US010485993B2

(12) United States Patent
Goer et al.

(10) Patent No.: US 10,485,993 B2
(45) Date of Patent: Nov. 26, 2019

(54) LOW ENERGY ELECTRON BEAM RADIATION SYSTEM THAT GENERATES ELECTRON BEAMS WITH PRECISELY CONTROLLED AND ADJUSTABLE PENETRATION DEPTH USEFUL FOR THERAPEUTIC APPLICATIONS

(71) Applicant: INTRAOP MEDICAL CORPORATION, Sunnyvale, CA (US)

(72) Inventors: Donald A. Goer, Sunnyvale, CA (US); Alexandre S. Kretchetov, San Jose, CA (US); David H. Whittum, Sunnyvale, CA (US); James A. Nelson, Newark, CA (US)

(73) Assignee: INTRAOP MEDICAL CORPORATION, Sunnyvale, CA (US)

( * ) Notice: Subject to any disclaimer, the term of this patent is extended or adjusted under 35 U.S.C. 154(b) by 0 days.

(21) Appl. No.: 16/080,198

(22) PCT Filed: Mar. 1, 2017

(86) PCT No.: PCT/US2017/020191
§ 371 (c)(1),
(2) Date: Aug. 27, 2018

(87) PCT Pub. No.: WO2017/151763
PCT Pub. Date: Sep. 8, 2017

(65) Prior Publication Data
US 2019/0054318 A1 Feb. 21, 2019

Related U.S. Application Data

(60) Provisional application No. 62/302,077, filed on Mar. 1, 2016.

(51) Int. Cl.
*A61N 5/10* (2006.01)

(52) U.S. Cl.
CPC ......... *A61N 5/1067* (2013.01); *A61N 5/1049* (2013.01); *A61N 2005/1059* (2013.01);
(Continued)

(58) Field of Classification Search
CPC .......... A61N 2005/1095; A61N 5/1067; A61N 2005/1059; A61N 2005/1074; A61N 2005/1089; A61N 5/1049
See application file for complete search history.

(56) References Cited

U.S. PATENT DOCUMENTS 3,820,035 A   6/1974   Meddaugh
3,852,610 A   12/1974  McIntyre
(Continued)

FOREIGN PATENT DOCUMENTS

WO   2013/134597 A1   9/2013

OTHER PUBLICATIONS

PCT/US2017/020191, Intraop Medical Corporation, International Search Report, dated May 24, 2017, 4 pages.
(Continued)

*Primary Examiner* — David P Porta
*Assistant Examiner* — Fani Boosalis
(74) *Attorney, Agent, or Firm* — Kagan Binder, PLLC

(57) ABSTRACT

The present invention provides electron beam therapies with improved feedback control that delivers controlled and adjustable doses of electron beam radiation to variable shallow depths with little radiation exposure to both nearby tissues and tissues below the target. In order to control radiation to accurately penetrate to shallow depths and to allow the radiation to be adjusted to other depth settings in very small or even continuous increments, the present invention senses a plurality of different electron beam characteristics and then uses these to derive a composite characteristic, or analog, of the electron beam energy. The composite
(Continued)

analog provides a strong correlation to energy that allows this precision. In another aspect, the present invention relates to implementing this feedback control by adjusting power levels used to establish the electron beam. In other embodiments, feedback control adjusts absorbing components with variable electron beam absorption depending on how such components are presented to the electron beam.

22 Claims, 19 Drawing Sheets

(52) U.S. Cl.
 CPC .............. *A61N 2005/1074* (2013.01); *A61N 2005/1089* (2013.01); *A61N 2005/1095* (2013.01)

(56) References Cited

U.S. PATENT DOCUMENTS

| | | | |
|---|---|---|---|
| 5,321,271 | A | 6/1994 | Schonberg |
| 5,418,372 | A | 5/1995 | Schonberg et al. |
| 5,661,377 | A | 8/1997 | Mishin et al. |
| 6,087,664 | A | 7/2000 | Gripp et al. |
| 6,864,633 | B2 | 3/2005 | Trail et al. |
| 7,339,320 | B1 | 3/2008 | Meddaugh et al. |
| 7,400,093 | B2 | 7/2008 | Salop et al. |
| 8,111,025 | B2 | 2/2012 | Whittum et al. |
| 8,198,587 | B2 | 6/2012 | Whittum et al. |
| 8,269,197 | B2 | 9/2012 | Goer et al. |
| 8,719,398 | B2 | 5/2014 | Qian et al. |
| 8,791,437 | B2 | 7/2014 | Felici et al. |
| 9,030,134 | B2 | 5/2015 | Whittum et al. |
| 9,040,945 | B1 | 5/2015 | Hayman |
| 9,308,395 | B2 | 4/2016 | Adler, Jr. et al. |
| 9,746,581 | B2 | 8/2017 | Whittum et al. |
| 9,757,593 | B2 | 9/2017 | Adler et al. |
| 2009/0314590 | A1 | 12/2009 | Dagh et al. |
| 2011/0017920 | A1* | 1/2011 | Goer ................. A61N 5/10 250/396 R |
| 2014/0091238 | A1 | 4/2014 | Miyashita et al. |

OTHER PUBLICATIONS

Almond et al., "The calibration and use of plane-parallel ionization chambers for dosimetry of electron beams: An extension of the 1983 AAPM protocol report of AAPM Radiation Therapy Committee Task Group No. 39" Medical Physics vol. 21, No. 8, (1994) pp. 1251-1260; doi: 10.1118/1.597359.

McLaughlin, David, "Energy spectra comparisons for matched clinical electron beams on Elekta linear accelerators using a permanent magnet spectrometer" (2013). LSU Master's Theses, pp. 1-173 103; https://digitalcommons.lsu.edu/gradschool_theses/103.

B. Grosswendt, "Determination of Electron Depth-Dose Curves for Water, ICRU Tissue, and PMMA and Their Application to Radiation Protection Dosimetry" Radiation Protection Dosimetry, vol. 54, Issue 2, (1994) pp. 85-97, https://doi.org/10.1093/oxfordjournals. rpd.a082321.

Wambersi et al., "Medical Applications of Electron Linear Accelerators" In: Turner S (ed) CERN Accelerator School (CAS): Cyclotron, linacs and their applications, CERN 96-02, (1996) CERN, Geneva, pp. 229-248.

Whittum, "Microwave Electron Linacs for Oncology", Reviews of Accelerator Science and Technology, vol. 2 (2009) pp. 63-92.

AAPM Report No. 63, Radiochromic Film Dosimetry, "Radiochromic film dosimetry: Recommendations of AAPM Radiation Therapy Committee Task Group 55" (1998), pp. 1-25, Reprinted from Medical Physics, vol. 25, Issue 11, Nov. 1998.

Price et al., In vivo dosimetry with optically stimulated dosimeters and RTQA2 radiochromic film for intraoperative radiotherapy of the breast Medical Physics 40 (9), pp. 091716-1-091716-9 (2013); doi: 10.1118/1.4819825.

Tabata, "Backscattering of Electrons from 3.2 to 14 MeV*", Postprint, re-edited for inclusion in T. Tabata, edited with commentary, The Collected Works of Tatsuo Tabata vol. 3, IDEA-TR 7 (2017), of the paper published in the Physical Review, vol. 162, Issue 2, Oct. 10, 1967, pp. 336-347 (doi:10.1103/PhysRev.162.336).

Kenneth F. Korai and Allan J. Cohen, "Empirical Equations for Electron Backscattering Coefficients, NASA Technical Note", NASA TN D-2909, pp. 1-19 (1965); https://ntrs.nasa.gov/search.jsp?R= 19650017673 2019-06-20T12:37:48+00:00Z.

Bengt E. Bjarngard, et al., "Electron scattering and collimation system for a 12-MeV linear accelerator", Med. Phys. vol. 3, No. 3, May/Jun. 1976 pp. 153-158.

Sung-Joon Ye, et al., "Monte Carlo techniques for scattering foil design and dosimetry in total skin irradiations", Med. Phys. 32 (6), Jun. 2005, pp. 1460-1468.

Prof.P.G.Mahajan et al., "Basic Operation & Applications of Van de Graaff Generator" IJSRE vol. 05, Issue 05, May 2017, pp. 6395-6399; DOI: http://dx.doi.org/10.18535/ijsre/v5i05.04.

Karzmark, "Advances in linear accelerator design for radiotherapy" Medical Physics, vol. 11, No. 2, Mar./Apr. 1984, pp. 105-128.

Nakagawa et al., "Dosimetry of leakage doses from a mobile accelerator for IORT and legal issues for its clinical use in Japan" Int J Clin Oncol (1999) 4, pp. 215-219.

Purdy et al., "Dual Energy X-Ray Beam Accelerators in Radiation Therapy: An Overview" Nuclear Instruments and Methods in Physics Research B10/11 (1985) pp. 1090-1095.

D. Goer, Linear Accelerator, Medical , Encyclopedia of Medical Devices and Instrumentation, 1988, John Wiley & Sons, vol. 3, pp. 1772 1800.

Muluta et al., "Intraoperative Electron Radiotherapy (IOERT) as an Alternative to Standard Whole Breast Irradiation: Only for Low-Risk Subgroups?" Breast Care (2014) 9, pp. 102-106; DOI: 10.1159/ 000362392.

Silverstein et al., "Intraoperative Radiation Therapy: A Critical Analysis of the ELIOT and TARGIT Trials. Part 1—Eliot" Ann Surg Oncol, Jun. 23, 2014, Published online: Aug. 27, 2014, pp. 1-6; DOI 10.1245/ s10434-014-3998-6.

Silverstein et al., "Intraoperative Radiation Therapy: A Critical Analysis of the ELIOT and TARGIT Trials. Part 2—TARGIT" Ann Surg Oncol, Jun. 23, 2014, Published online: Aug. 20, 2014, pp. 1-6; DOI 10.1245/ s10434-014-3999-5.

Meurk et al., "The Mobetron: A New Concept for IORT" Vaeth JM (ed): Intraoperative Radiation Therapy in the Treatment of Cancer, Front Radiat Ther Oncol. Basel, Karger, 1997, vol. 31 , pp. 65-70.

Beddar et al., "Intraoperative radiation therapy using mobile electron linear accelerators: Report of AAPM Radiation Therapy Committee Task Group No. 72" Med. Phys. 33, (2006) pp. 1476-1489.

Khan et al., AAPM Report No. 32, Clinical electron-beam dosimetry: Report of AAPM Radiation Therapy Committee Task Group No. 25, Med. Phys., vol. 18, Issue 1, (1991) pp. 73-109.

Almond et al., "AAPM's TG-51 protocol for clinical reference dosimetry of high-energy photon and electron beams" Med. Phys. 26 (Sep. 9, 1999) pp. 1847-1870.

NanoDot™—Dosimetry Badges | Landauer,https://www.landauer. com/product/nanodot, (2019) pp. 1-2.

IntraOp, Mobetron® 2000 Product Specification (Sep. 2016) pp. 1-16.

Varian, SIP Data Sheet, Linatron XP 950 kV Portable X-Band X-Ray Source (May 2016) pp. 1-2.

* cited by examiner

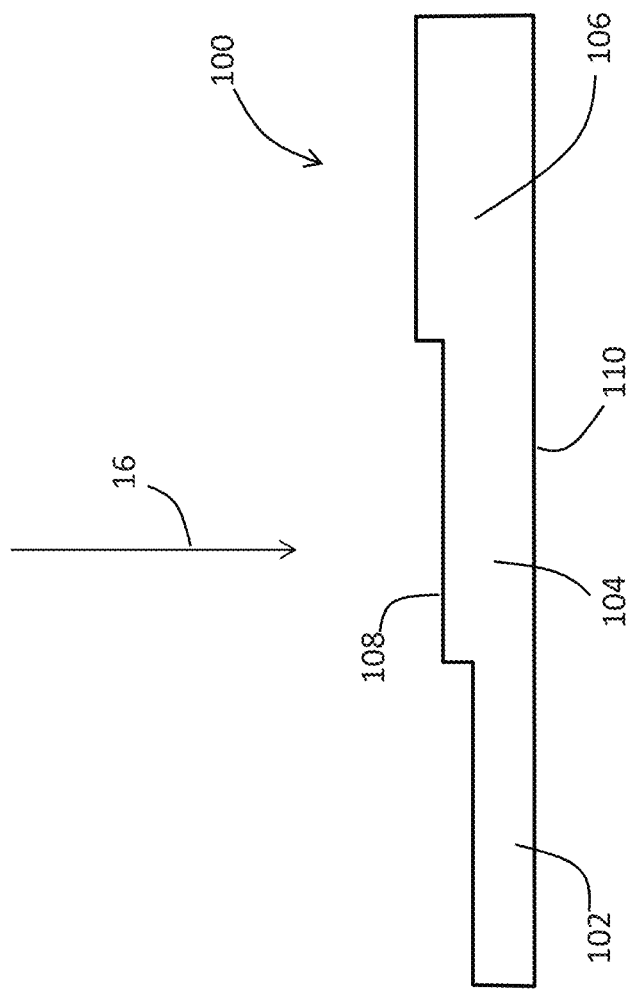

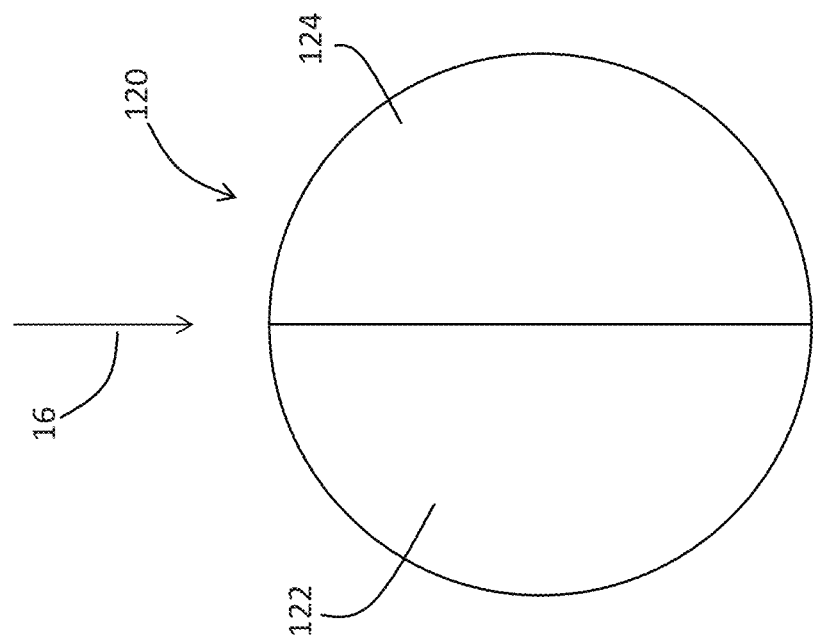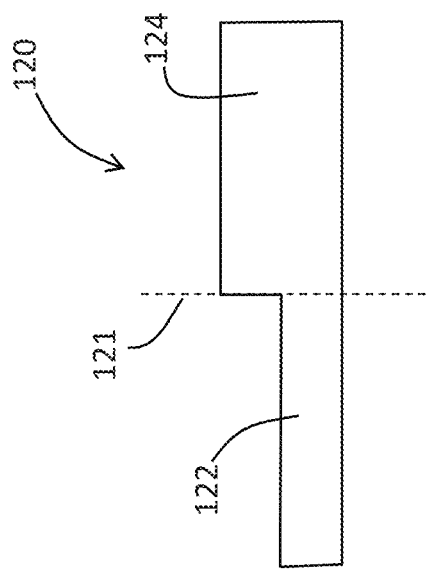

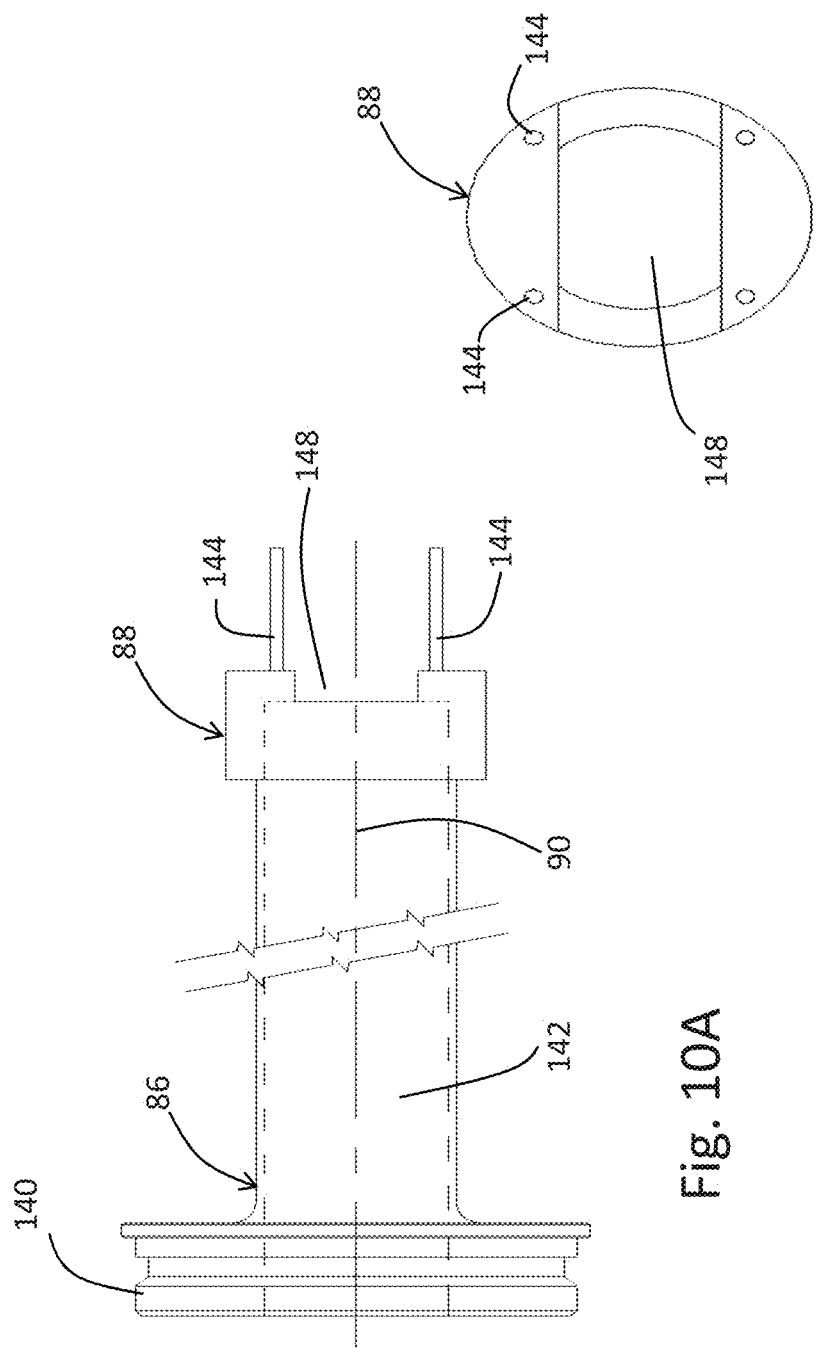

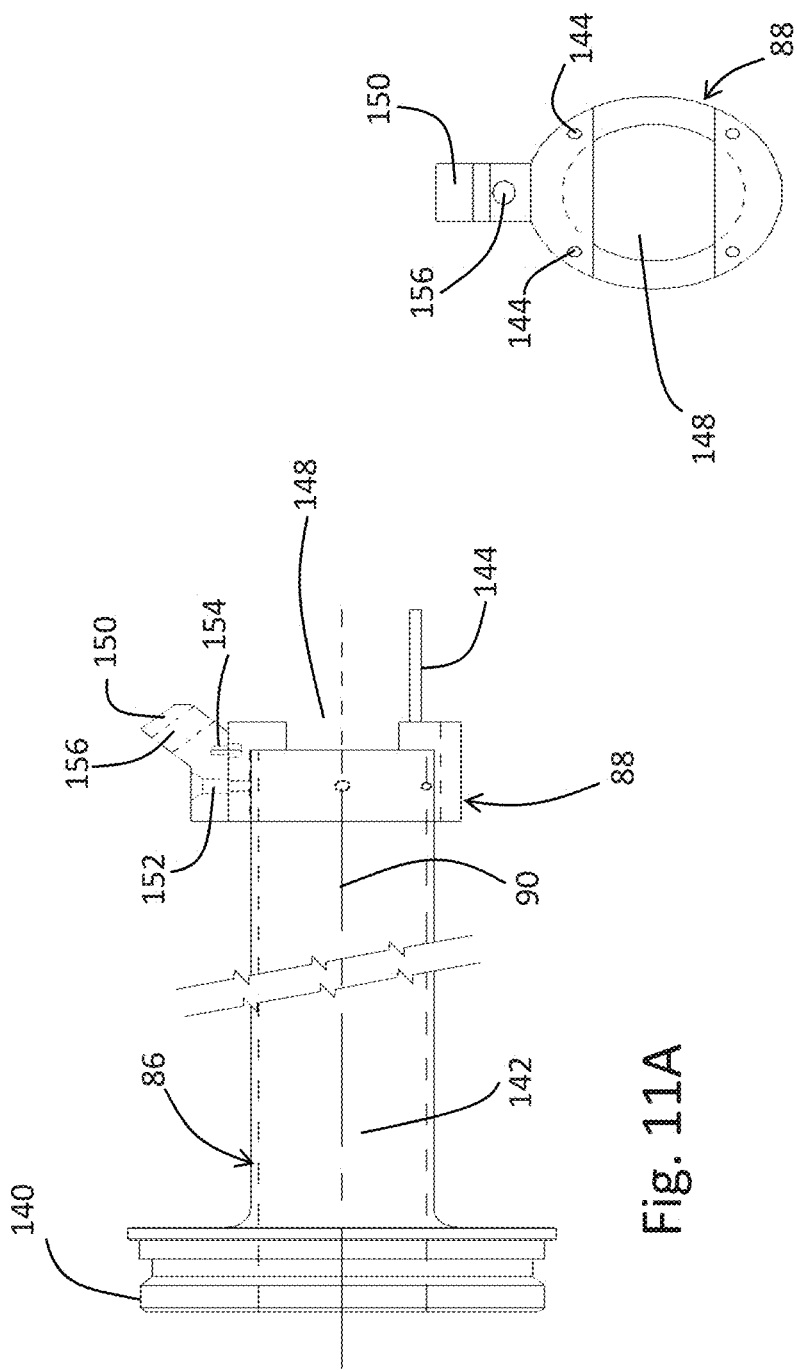

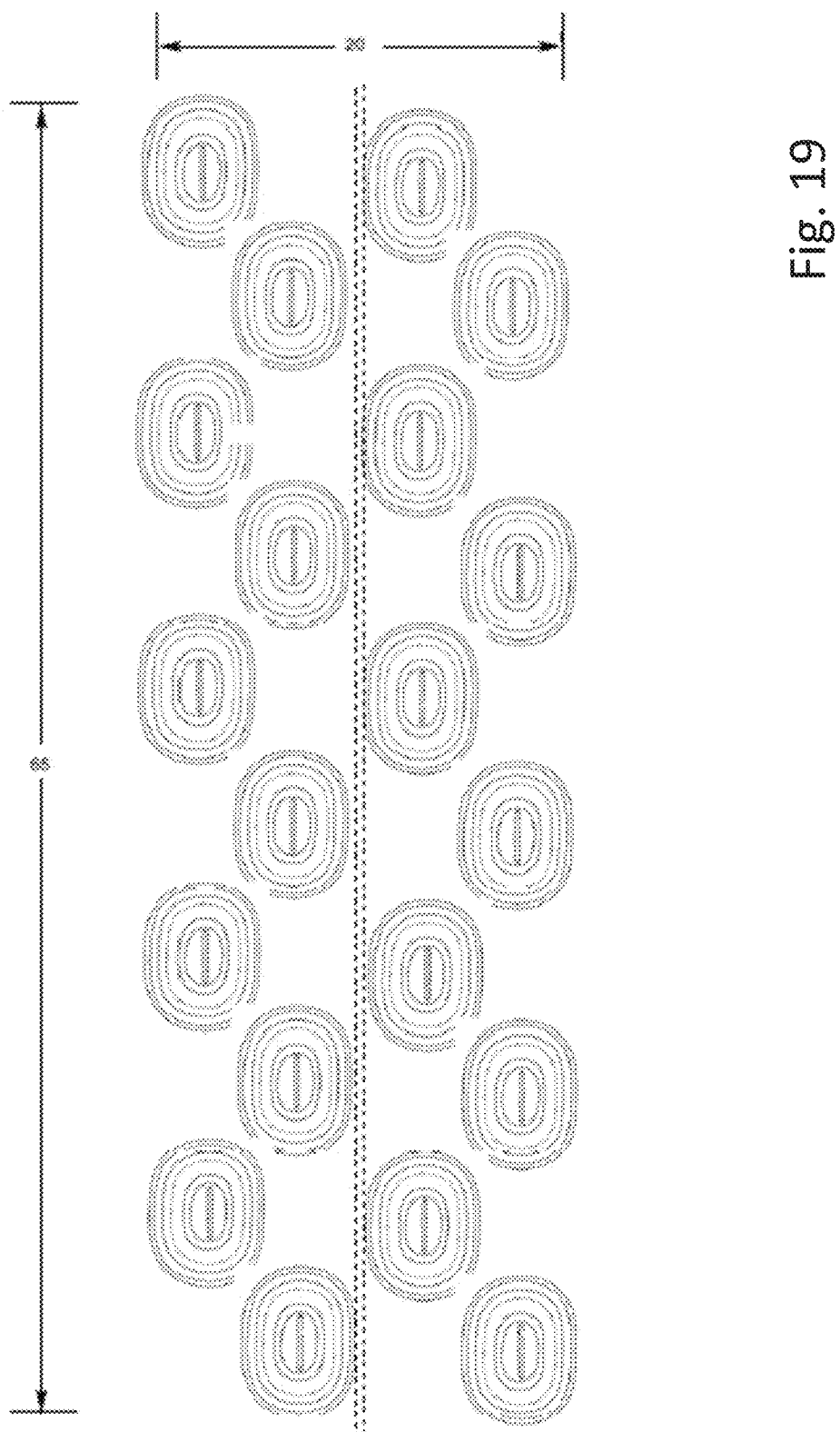

LOW ENERGY ELECTRON BEAM RADIATION SYSTEM THAT GENERATES ELECTRON BEAMS WITH PRECISELY CONTROLLED AND ADJUSTABLE PENETRATION DEPTH USEFUL FOR THERAPEUTIC APPLICATIONS

PRIORITY CLAIM

This application claims priority to International Application No. PCT/US2017/020191, filed on Mar. 1, 2017, which in turn claims priority under 35 USC 119 to U.S. Provisional Patent Application No. 62/302,077, filed Mar. 1, 2016, the entireties of which are respectively incorporated herein by reference for all purposes.

FIELD OF THE INVENTION

The present invention relates to the field of linear, straight through electron beam machines and methods used for therapeutic uses. More particularly, the present invention relates to linear, straight through electron beam machines that incorporate a feedback strategy that allows the electron beam to be generated with controlled and adjustable penetration depth for therapeutic radiation applications.

BACKGROUND OF THE INVENTION

Therapeutic radiation often is designed to penetrate deeply into a patient, as most targets for therapeutic radiation are located well below the surface. Even therapeutic radiation used to treat lesions on the skin surface still can penetrate several centimeters below the surface. To allow unaffected (normal) tissue to recover, the therapeutic radiation is generally delivered in many daily treatments, called fractions. Such fractional treatments rely on the principle that well-oxygenated normal tissues will repair and recover from radiation damage more quickly than the tissues being targeted by the therapeutic radiation. Even when the therapeutic radiation is delivered in fractions, permanent radiation damage to healthy tissues surrounding the radiation site could still occur.

It is therefore desirable to provide a radiation device that deposits a substantial portion of its radiation at the target tissues and much less radiation to the normal tissues surrounding the target. This is especially challenging for targets that are at or close to the surface. It is also desirable to avoid radiation exposure to healthy tissues that are adjacent to the target, irrespective of the depth of the target.

One example of the need for radiation devices capable of producing radiation doses at shallow depths is when treating scars and/or in ameliorating scar formation. Surgery inevitably produces scarring as a result of creating wounds. When wounds heal, there is an immediate inflammation of the wound site in which neutrophils infiltrate the wound which can cause excessive tissue loss in the scar area, leaving an area devoid of a matrix that is subsequently replaced with scar tissue through collagen synthesis and proliferation of other components in the extracellular matrix.

Radiation has been known to ameliorate this proliferation. However, in many conventional treatments radiation may not be provided until days or weeks after the surgery because it is logistically difficult to irradiate wounds in the operating room or the emergency room where most wounds are created. In scar irradiation, it is often desirable to irradiate to the depth of the dermis, sparing the epidermis as much as possible. The dermis varies in thickness and depth, depending on the anatomy. This requires a radiation device capable of irradiating at varying shallow depths of 1 mm to 10 mm with high precision, depending on the body location of the scar. For optimal scar treatment, an electron beam machine would have enough precision in order to achieve a range of penetration depth settings in increments of 2 mm or less, or even 1.5 mm or less, or even 1 mm or less increments.

Conventional electron beam machines, though, tend to produce beams whose tolerances can vary by +/−2 mm or more in terms of corresponding penetration depth. Such a large variation makes fine adjustments impossible, because the variation of the electron beam is as big as and is even larger than the desired tuning increments. Such a coarse variation means that conventional machines have a coarse precision with the result that electron beam energy adjustments are typically in relatively large increments of no less than 1 cm or even larger increments between penetration depth settings. The result is that conventional electron beam machines do not have as much precision as would be desired for improved scar treatments.

Another example is in vascular surgery, where repair of femoral and carotid artery blockages presents a high probability of restenosis. Irradiating the sutured junction of the repaired artery can prevent restenosis by inhibiting excess growth from the blood vessels walls. However, to be most effective, this radiation should be delivered at the time of the surgery, or shortly thereafter, to inhibit the excessive growth caused by the vessel repair while avoiding damage to tissues overlying or surrounding the blood vessels. Irradiation of a blood vessel may occur after anastomosis in some embodiments. Care desirably must be taken that the radiation is confined to the vessel walls and does not extend to nerves and tissues beneath the vessel.

Another example is in abdominal surgery, where low energy electron radiation may inhibit adhesion of surgically manipulated tissues, a common result of surgery. Adhesions can cause patient pain or discomfort and make re-operations at a later date more difficult.

Again, conventional electron beam machines suffer from a lack of precision to allow such finely focused therapies such as with respect to vascular or abdominal surgeries. This reinforces the strong desire to produce more stable electron beams to make it possible to achieve precise, shallow, penetration depths in fine increments.

X-ray radiation is another type of therapeutic radiation, X-ray radiation, though, is undesirable for these shallow depth therapeutic uses, as it penetrates deeply and can damage underlying tissues. Low energy x-rays (30 to 50 KV) have a limited penetration, but still could result in excessive dose delivered to the skin and epidermis. Electron beam radiation, therefore, is a better candidate for these shallow therapies than x-rays. Yet, there remains a need for new methods and devices for administering targeted electron beam radiation to patients in need thereof.

In principle energy can be controlled by means of chromatic magnetic elements in the beamline. One example is a dipole magnet system configured as a spectrometer. For a straight through beam, another approach is to look at "yield", i.e., production of ionizing radiation per unit beam current. Use of a "yield servo" is known in the art for X-ray machines, which impact an electron beam on a bremsstrahlung conversion target to produce X-Rays. The intensity of X-Rays may be monitored by means of an ionization chamber downstream. Use of ion chambers for dosimetry is known in the art, both for reference dosimetry and machine dosimetry. See P. R. Almond, et al., The calibration and use of plane-parallel ionization chambers for dosimetry of electron beams, Med. Phys. 21, (8), August 1994 ("TG-39"); Raymond D. McIntyre, Transmission Ion Chamber, U.S. Pat. No. 3,852,610.

In the case of x-ray machines, the ratio of ionization chamber current collected to average beam current incident on a target provides an analog of energy, varying as roughly energy cubed. A yield servo for X-Rays is based on bremsstrahlung X-Ray yield from a target that destructively intercepts the electron beam. Bremsstrahlung is electromagnetic radiation produced by the acceleration or especially the deceleration of a charged particle after passing through the electric and magnetic fields of a nucleus. This approach works well in the x-ray context, because radiative yield varies as energy cubed. With the large currents (e.g., 100 mA) typical of x-ray machines, signals are robust. However, it is not possible to use such a conversion target for an electron beam, as the beam would be destroyed. In fact, a requirement on beam monitors and other beam line devices for a straight-through electron machine is to avoid bremsstrahlung contamination in the treatment field. This poses a technical challenge of how to monitor the electron beam energy without interfering with beam quality in a straight-through electron machine.

Electron beam machines, as a result, are different than x-ray machines and principles for highly precise control of electron beam settings and fine adjustment to other settings is not yet known in the field of shallow therapeutic treatments. For electron beam machines of variable energy, two approaches are used in the field today to control electron beam energy. One is the spectrometer-based approach, where dispersion is generated to spread the beam out in a radial dimension and pass the beam through water-cooled slits of width corresponding to 6% in energy. The beam is then recombined by the magnetic optics and, directed toward the target volume. This approach generates background radiation at the slits, and other parts of the bend magnet system. This necessitates additional shielding, additional strengthening of mechanical members to hold the shielding, and, altogether a 17,000 lb machine that is not mobile and requires a specially designed vault with concrete walls that are several feet thick. The other approach is the straight-through electron beam machine, as with the MOBETRON unit commercially available from IntraOp Medical Corporation. Straight-through electron beam systems are designed to produce very low stray radiation and thus can operate safely in unshielded environments. Examples of such machines are described in U.S. Pat. Nos. 5,321,271 and 5,418,372. Instead, system parameters are tightly specified and deviation from an acceptance range results in interlock and beam off.

The MOBETRON system stably operates at three energies 6, 9 and 12 MeV without closed loop feedback. Energy stability is maintained through special rf-circuitry or through other means such as is described in U.S. Pat. No. 5,661,377, but there is no energy servo to control and modulate the electron beam other than to set the beam energy at these three levels Instead, system parameters are tightly specified and deviation from an acceptance range results in interlock and beam off.

There is a need for a radiation device that is capable of delivering more stable, electron beam radiation with higher precision to many shallow depths in fine increments with little radiation exposure to both nearby tissues and tissues below the target. In order to control radiation to accurately penetrate to shallow depths and to allow the radiation to be adjusted to other depth settings in very small or even continuous increments, improved strategies to stabilize and control the penetration depth of the electron beam are needed.

SUMMARY OF THE INVENTION

The present invention provides electron beam systems and therapies that provide electron beams with improved stability and precision. In exemplary embodiments, the electron beam machines of the present invention are compact, lightweight, self-shielded machines that use lower electron beam energies suitable for shallower therapies. Unlike conventional machines that weigh several thousand pounds or even several tons, the exemplary embodiments of the present invention are compact and light enough to be deployed such as by ceiling mounting, wall mounting, horizontal surface mounting, or on mobile carts. These embodiments are easily deployed on conventional articulating arms and can be moved around or articulated to provide treatment in intraoperative or other settings. The machines have great flexibility in beam shaping due to the use of applicators or integrated collimator/applicator components described below. With such a stable electron beam, energy changes, and hence penetration depth settings, are easily tuned in fine increments by pre-set energy levels, electronic feedback techniques, and/or the mechanical interposition of selected absorbers to modify or tune the beam to correspond to a desired penetration depth.

The present invention provides improved feedback control that delivers more stable, controlled and adjustable doses of electron beam radiation to variable shallow depths with little radiation exposure to both nearby tissues and tissues below the target. In order to control radiation to accurately penetrate to shallow depths and to allow the radiation to be adjusted to other depth settings in very small or even continuous increments, the present invention senses a plurality of different electron beam characteristics and then uses these to derive a composite characteristic, or analog, of the electron beam energy. Although the individual characteristics do not, on their own, allow precision control of electron beam energy level and adjustment, the composite analog does provide a strong correlation to energy that allows this precision. Accordingly, one aspect of the present invention is to provide improved feedback strategies to control and adjust electron beams. In another aspect, the present invention relates to implementing this feedback control by adjusting power levels used to establish the electron beam. In other embodiments, feedback control automatically adjusts or helps guide manual adjustment or selection of absorbing components that are presented to the electron beam. In other embodiments, feedback control can be implemented by adjusting other system variables such as gun voltage, microwave frequency, or the like.

Measurement of an electron beam spectrum for feedback control has been challenging. See Energy Spectra Comparisons for Matched Clinical Electron Beams on Elekta Linear Accelerators Using a Permanent Magnet Spectrometer, David James McLaughlin, M. S. Thesis, LSU (December 2013)(http://etd.lsu.edu/docs/available/etd-09272013-155509/unrestricted/McLaughlin_MS_Thesis.pdf). The feedback system of the invention appreciates that it is not necessary to monitor the beam energy spectrum in detail in order to provide precise penetration depth. Rather the system can monitor drift or fluctuation in an analog of beam energy, and act upon system parameter(s) whose variation impacts the electron beam spectrum so as to maintain a highly stable, accurately, and precisely tunable penetration depth. Examples of such system parameter drift or fluctuation include fluctuation in voltage to or from a modulator or gun power supply; thermal variations that change performance of system components such as a magnetron, circulator, or accelerator, and/or mechanical variations that result from rotation or translation of the system; and/or other system drifts that cause drift in beam energy.

The improvement in stability is significant. The feedback control and various options to tune the beam as delivered to a treatment site creates a beam with so much stability that the penetration depth can be adjusted in continuous or fine increments of 2 mm or less, even 1.5 mm or less, or even 1 mm or less. In exemplary modes of practice, the penetration depth can be adjusted by increments in a range from 0.3 mm to 2 mm, preferably 0.3 mm to 1.5 mm, more preferably 0.5 mm to 1 mm. A particularly preferred embodiment adjusts penetration depth in increments of about 1 mm. In contrast, conventional electron beam machines produce electron beams whose variation is as large and even larger than these increments. As a consequence, conventional machines have been limited to making much coarser adjustments of penetration depth, such as increments of 1 cm or larger. This means that illustrative embodiments of the present invention would offer a 10-fold improvement to fine tune penetration depth. In performing these irradiations, the present invention accurately sets and adjusts electron beam energy at the target site to a desired level within an operating range such as from 0.1 MeV to 6 MeV in order to provide the desired penetration depth.

The invention is able to control and adjust lower energy megavoltage beams for irradiation of patients for or as an adjunct to surgery or other treatments. For example, principles of the present invention can be used to carry out a wide variety of electron beam therapies and other treatments on a wide variety of treatment sites in or on a patient in a wide variety of treatment settings. In illustrative modes of practice, electron beam machines incorporating principles of the present invention do not need to be deployed in a radiation-shielded vault but may be deployed in an ordinary room, such as a surgical suite, an outpatient clinic office, emergency rooms, or in other areas that do not have additional radiation shielding. The invention may also be employed outdoors and may operate for a time without benefit of externally provided power. This makes the present invention suitable for intraoperative therapies and treatments. As a result, the irradiation according to the present invention may be applied promptly before, during, or after surgery. Due to the time-sensitive nature of the therapeutic effect of electron beams post-incision, it is beneficial in the practice of the present invention to apply the electron beam immediately during, or after surgery. For some treatments, it may be beneficial to apply the radiation before a surgery. For some treatments, for example, treatment of restenosis, it is beneficial to apply the electron beam during surgery.

Many features of the present invention confine the radiation treatment field to a narrow or confined area and, along with using lower electron beam energies, minimize dose to healthy or non-involved tissues. For example, the present invention can accommodate the depth sensitive nature of the configuration of the epidermis to the dermis, as well as other similar structures. In general, the thickness of the epidermis varies from patient to patient and among different sites on a given patient. Thus the first rigorous indication of epidermal thickness may be obtained in the course of performing a surgical procedure. If the surgeon or therapist should determine that the epidermal thickness is, for example, 3 mm, they would ideally be in a position to quickly provide radiation of the appropriate depth-dose characteristic on the spot. The present invention is able to treat the dermis while sparing the epidermis because the penetration depth of irradiation can be controlled and adjusted in fine or continuous increments of 2 mm or better or even 1 mm or better. Being able to control depth penetration with this incremental precision heretofore has been an unknown feat in the field of electron beam therapy.

In one aspect, the present invention relates to an electron beam radiation system useful to irradiate a target site on a patient with electron beam radiation dose having a controlled and adjustable penetration depth, said system comprising:
  a) an electron beam aimed at the treatment site, said electron beam having an adjustable and controllable electron beam energy adjusted to correspond to a desired penetration depth; and
  b) a control system configured to permit controlling the electron beam (such as to control penetration depth, interlock protocols, and the like), wherein the control system comprises a feedback system, comprising:
    i) first and second sensors presented to the electron beam in a manner effective to detect first and second characteristics of the electron beam;
    ii) a controller that uses the first and second characteristics to derive an analog characteristic and that uses information comprising the analog characteristic and a reference value to derive an error signal, and wherein the controller generates a control signal from the error signal and causes the control signal to control the penetration depth of the electron beam.

In another aspect, the present invention relates to an electron beam radiation system useful to irradiate a target site on a patient with an electron beam radiation dose having a controlled and adjustable penetration depth, said system comprising:
  a) a power source providing a power output;
  b) a microwave source that receives the power output from the power source and emits microwave energy;
  c) a microwave network that receives the microwave energy from the microwave source;
  d) an electron beam source that emits an electron beam;
  e) an accelerator system configured to receive the electron beam from the electron beam source and to receive the microwave energy from the microwave network in a manner effective to accelerate the electron beam toward the target site;
  f) a collimator that receives and shapes the accelerated electron beam; and
  g) a feedback control system, comprising:
    1) a first electron beam sensor that measures a first characteristic of the accelerated electron beam;
    2) a second beam sensor that measures a second characteristic of the accelerated electron beam that is different from the first characteristic; and wherein:
    the feedback control system uses first and second signals from the first and second sensors to derive an analog characteristic of electron beam energy; and
    the feedback control system uses the analog of electron beam energy to generate a control signal that controls the electron beam energy at a level that is in the range from 0.1 MeV to 6 MeV and that corresponds to a desired penetration depth at the target site.

In another aspect, the present invention relates to an electron beam radiation system useful to irradiate a target site with electron beam radiation dose having an adjustable penetration depth, said system comprising:

a. an electron beam directed at the target site, said electron beam having an adjustable and controllable electron beam energy adjusted to correspond to a desired penetration depth; and
b. a library of electron beam absorbers configured to provide stepwise tuning of an electron beam in increments of 2 mm or less, wherein at least one electron beam absorber is presented to the electron beam in a manner to reduce the electron beam energy to control the penetration depth of the electron beam dose delivered to the target; and
c. a feedback system configured to stabilize the penetration depth of a linearly accelerated, straight through electron beam having an electron beam energy, said system providing a control signal derived from a plurality of sensed electron beam characteristics that in combination correlate to the electron beam energy.

In another aspect, the present invention relates to a method for irradiating a surgical incision site made at a time of a surgery, comprising the step of using the electron beam radiation system of Claim 1, 17, or 18 to deliver an electron beam radiation dose at the surgical incision site within a time period of less than 5 hours of the time of the surgery, wherein the electron beam delivered to the surgical incision site has an electron beam energy of 0.1 MeV to 6 MeV.

In another aspect, the present invention relates to a method for irradiating a target site, comprising the step of using the electron beam radiation system of Claim 1, 17, or 18 to intraoperatively deliver an electron beam radiation dose at target site, wherein the electron beam delivered to the surgical incision site has an electron beam energy of 0.1 MeV to 6 MeV at the target site.

In another aspect, the present invention relates to a method for irradiating a target site on a patient with an electron beam radiation dose having a controlled and adjusted penetration depth, comprising the steps of
a) aiming an electron beam at the target site on the patient, wherein the electron beam has an adjustable and controllable electron beam energy adjusted to correspond to a desired penetration depth; and
b) using a control system to adjust the electron beam to an energy effective to correspond to the desired penetration depth;
c) using the control system to monitor the electron beam and to use at least first and second sensed characteristics to derive an analog of electron beam energy;
d) using the control system to derive an error signal from information comprising the analog characteristic of the electron beam energy and a reference value; and
e) using the control system to generate a control signal that controls the electron beam energy.

BRIEF DESCRIPTION OF THE DRAWINGS

FIG. 8 schematically illustrates one embodiment of an absorber useful for tuning electron beam energy in the system of FIG. 1.

FIG. 9A schematically illustrates a side view another embodiment of an absorber useful for tuning electron beam energy in the system of FIG. 1.

FIG. 9B schematically illustrates a top view of the absorber of FIG. 9A.

FIG. 10A shows side views of embodiments of an applicator and field defining shield useful in the units of FIGS. 2 and 3.

FIG. 10B shows and end view of the applicator and field defining shield of FIG. 10A.

FIG. 11A shows side views the applicator and field defining shield of FIG. 10A fitted with an endoscope mount.

FIG. 11B shows and end view of the applicator, field defining shield, and endoscope mount of FIG. 11A.

FIG. 19 shows a scar pattern to be used in a hypothetical clinical study protocol, wherein the pattern includes an array of the dose distribution profile of FIG. 18, and wherein the field dimensions are shown in centimeters.

DETAILED DESCRIPTION OF PRESENTLY PREFERRED EMBODIMENTS

The embodiments of the present invention described herein are not intended to be exhaustive or to limit the invention to the precise forms disclosed in the specification and Figures. Rather a purpose of the illustrative embodiments chosen and described is so that the appreciation and understanding by others skilled in the art of the principles and practices of the present invention can be facilitated. While illustrative embodiments of the present invention have been shown and described herein, the skilled worker will appreciate that such embodiments are provided by way of example and illustration only. Numerous variations, changes, and substitutions will now occur to those skilled in the art without departing from the invention. No unnecessary limitations are to be understood therefrom. The invention is not limited to the exact details shown and described, and any variations are included that are within the scope of the claims.

All patents, patent applications, and publications cited herein are incorporated by reference in their respective entireties for all purposes.

Figure 1:
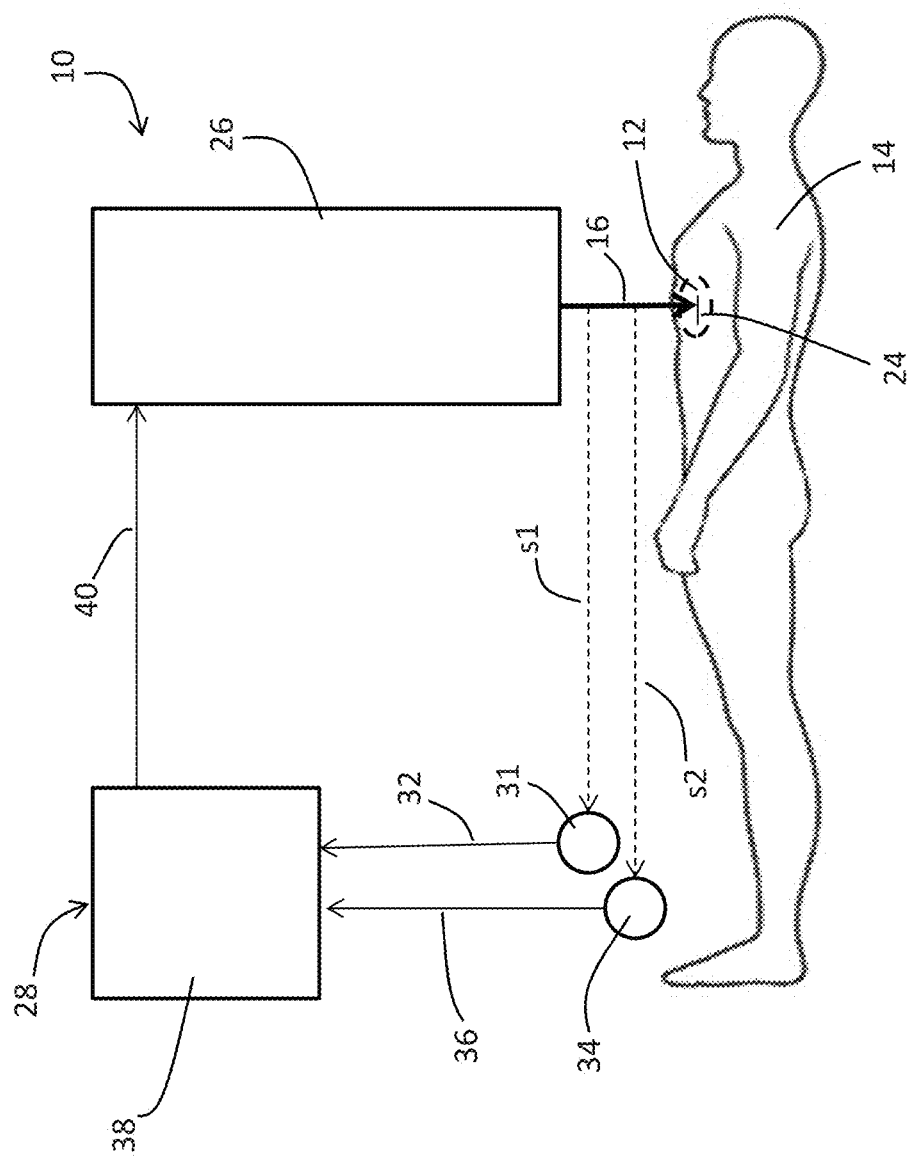
FIG. 1 schematically shows an illustrative embodiment of an electron beam radiation system of the present invention.

An exemplary embodiment of an electron beam (also referred to in the field of electron beam therapy as an "ebeam") radiation system 10 of the present invention is schematically shown in FIG. 1. Electron beam radiation system 10 is useful to irradiate a target site 12 on a patient 14 with an electron beam radiation dose having a controlled and adjustable penetration depth into the target site 12. As a consequence of irradiating target site 12 to the penetration depth, a target volume of patient 14 receives the desired irradiation dose.

System 10 is useful for irradiating a wide range of treatment sites anywhere in or on body or body parts of the patient 14. For example, external treatments may involve treating the ears, nose, face, forehead, scalp, back, shoulders, neck, arms, hands, chest, abdomen, pelvic region, legs, or feet. Internal treatment sites may include the brain, blood vessels and/or arteries, heart, lungs, liver, colon, stomach, gall bladder, intestinal tract, glands, muscles, ligaments, tendons, bone, or the like. Internal sites may be exposed during a surgery to make the target site more accessible during a treatment. Due to the ability to control the shape and aim direction of the electron beam aimed at the target site 12, system 10 is useful for treating target sites with a variety of shapes and contours.

Due to its compact nature, self-shielding capabilities, and/or mobility in many modes of practice, system 10 may be present and used intraoperatively at a location of a surgical or other care related procedure. This allows electron beam radiation to be applied before, during or promptly after surgery. Due to the time-sensitive nature of many therapeutic effects of electron beams, being able to apply irradiation intraoperatively in this manner is beneficial in many modes of practice. In some applications, electron beam radiation may be applied internally prior to closure of the wound, such as preventing surgical adhesions or in irradiating anastomosed blood vessels in vascular surgery to prevent restenosis. In some applications, such as scar amelioration, it is beneficial to irradiate the closed incision promptly. For example, system 10 can be used to deliver electron beam radiation dose(s) in a time period ranging from 0 to 24 hours, or even 0 to 5 hours, or even 0 to 1 hour, or even 0 to 30 minutes of the time of a surgery. This ability to apply irradiation treatments promptly is contrasted to treatments that use very large and immobile machines housed in separate, heavily-shielded environments that are remote from the treatment location. Radiation treatment in such large, remotely housed machines has been applied post-operatively after a delay of hours or days, thereby missing the opportunity to achieve the optimal benefits of electron beam radiation therapy.

System 10 is useful to carry out a wide range of treatments for which electron beam irradiation provides a treatment, benefit, or other desired effect for surgery or as an adjunct to surgery or other procedure. For example, system 10 may be used to treat dermatological conditions and/or to provide cosmesis. Exemplary applications in the dermatological field include prevention or treatment of scarring of the dermis including hypertrophic scarring, dermal fibroproliferative lesions, and benign fibrous tumors such as keloids. In some embodiments, electron beam radiation may be used to treat or prevent scar formation resulting from breast cancer surgical procedures or reduce the severity of scar formation in emergency room procedures. Other exemplary applications include treatment for internal conditions such as surgical adhesions and restenosis, as may occur when a blood vessel is treated for blockage. For example, system 10 may be used to irradiate the microvasculature of the surgical bed to reduce the probability of formation of surgical adhesions. As another example, as an adjunct to vascular surgery, system 10 may be used to treat the anastomosis of blood vessels such as the femoral artery, popliteal artery and carotid artery to help prevent restenosis.

For purposes of illustration. FIG. 1 shows system 10 being used to irradiate incised tissue proximal to a surgical incision 24 after wound closure in order to help reduce or prevent undue formation of scar tissue that otherwise could result as the incision subsequently heals.

Electron beam radiation system 10 of FIG. 1 generally includes an electron beam generation unit 26 that emits a linearly accelerated, straight through electron beam 16. The present invention allows the electron beam to be emitted with high stability and precision to achieve one or more desired penetration depth settings within a broad operating range. Not only can the electron beam be controlled to be at a particular penetration depth in the desired operating range, but the principles of the present invention allow the beam penetration depth to be rapidly adjusted and controlled in continuous or very small increments within the operating range. Being able to adjust and control electron beam penetration depth continuously or in small increments over the operating range provides tremendous flexibility to tailor dose and penetration depth to particular patient needs. This is a significant advantage over conventional machines that have only a limited number of energy settings and/or provide beams with less stability that are subject to coarser setting adjustments.

Penetration depth of an electron beam treatment means the $R_{80}$ penetration depth as determined in water according to the protocol described in Peter R. Almond et. al, "AAPM's TG-51 protocol for clinical reference dosimetry of high-energy photon and electron beams", Med. Phys. 26 (9), September 1999, pp. 1847-1870 (referred to in the industry as the AAPM TG51 report). Note that while the protocol focuses on electron beams with mean incident energies in the range from 5 MeV to 50 MeV, the same protocol is applicable for lower energies that are preferably used in the practice of the present invention. Additionally, the report provides a protocol to determine the R50 penetration depth. This is the depth in water at which the absorbed dose falls to 50% of the maximum dose. The same depth-dose data resulting from this protocol also provides the $R_{80}$ penetration depth, which is the penetration of an electron beam dose into a water phantom at which the dose drops to 80% of the maximum dose. The depth of dose maximum is referred to as Dmax. Beam and dosimetry calibration for evaluation of machine settings with respect to determining $R_{80}$ penetration depth in the practice of the present invention are defined in water using a 5 cm diameter, circular, 30 cm long zero degree tip angle applicator at a 50 cm source to skin distance (SSD). The output for a specific energy is measured at Dmax.

For example, if this test shows that a particular machine configuration yields an $R_{80}$ penetration depth of 2 cm, that configuration is deemed to provide that $R_{80}$, penetration depth at the target site 12. The machine may be calibrated or otherwise evaluated to determine a plurality of machine configurations to correspond to a corresponding plurality of penetration depths. At the time of a procedure, the care provider selects a particular penetration depth suitable for the procedure. The machine is set to the corresponding configuration. The procedure is then performed using principles of the present invention to deliver a stable and precise electron beam as the procedure is carried out.

Electron beam energy and penetration depth are strongly correlated. See B. Grosswendt, "Determination of Electron Depth-Dose Curves for Water, ICRU Tissue, and PMMA and Their Application to Radiation Protection Dosimetry," Radiat Prot Dosimetry (1994) 54 (2): 85-97. Depending on the embodiment, this relationship can be linear or nonlinear. Generally, higher penetration depth results from using electron beams with higher energy. In many embodiments, the electron beam energy delivered to the target site 12 is within a range from 0.1 MeV to 6 MeV, preferably 0.2 MeV to 5 MeV, more preferably 0.3 MeV to 4 MeV, and even more preferably 0.5 MeV to 2 MeV. In some modes of practice, an operation range from 1 MeV to 2 MeV would be optimal. In certain embodiments, the electron beam systems provide irradiation doses of up to about 20 Gy, such as up to about 15 Gy, up to about 10 Gy, up to about 5 Gy, or up to about 2 Gy. In certain embodiments, the electron beam systems provide radiation to the target site 12 at a rate of at least about 0.2 Gy/min, at least about 1 Gy/min at least about 2 Gy/min, at least about 5 Gy/min, or at least about 10 Gy/min.

System 10 of FIG. 1 offers many strategies for setting machine configurations to achieve desired penetration depths. As one example, a penetration depth is selected. System 10 produces a stable, precise electron beam. One or more electron beam absorbers (described further below) may then be selected to tune the beam as much as desired to provide the desired penetration depth. By having a library of absorbers with fine, stepwise differences in electron beam absorption, different penetration depths in fine increments can be delivered to treatment sites such as site 12. In the meantime, the feedback strategies of the present invention (described further below) are used to stabilize the electron beam with high precision prior to tuning by the absorber. To change to another penetration depth setting, one or more different absorbers are presented to the beam and/or the machine may be set to produce an electron beam with a different energy level that is presented to the one or more absorbers.

In other modes of practice, a penetration depth is selected. Without using an absorber to tune the electron beam, system 10 is set to the configuration that provides the electron beam energy level corresponding to the desired penetration depth. The feedback strategies of the present invention are used to stabilize the electron beam with high precision. To change to another penetration depth setting, the feedback system adjusts the electron beam in a corresponding fashion.

Thus, penetration depth is easily adjusted by electronically changing the machine configuration to tune the electron beam energy and/or by presenting selected absorber(s) to the beam. In these and other modes of practice, the feedback system can monitor one or more characteristics and then implement a control that turns off the beam if the beam is too far from a desired specification. This is a type of interlock control or protection.

The operating ranges of about 6 MeV or less generally are associated with lower levels electron beam energy in the field of electron beam therapy. Such energies, particularly those of about 4 MeV or less, are potentially more useful for shallow treatments, e.g., those in which the penetration depth (discussed further below) of the electron beam is in the range from about a fraction of 1 mm to several cm. For example, in illustrative embodiments, system 10 may implement irradiation to depths in the range from is 0.5 mm or less to about 4 cm, preferably 1 mm to about 3 cm, more preferably 1 mm to about 1 cm. In preferred modes of practice, the therapeutic penetration depth is limited to about 1.5 cm or less. Undue bremsstrahlung production can be avoided with careful attention to avoid unnecessary objects in the path of the electron beam. Certain objects are beneficially presented to the electron beam, such as scattering foils, windows, absorbers (described further below), sensors, ion chambers and the like.

The fact that system 10 provides lower energy electron beam irradiation with excellent, precision, control, adjustment, and stability offers many advantages. System 10 can confine the radiation treatment field to a narrow or confined area. This operating range and precision also makes it easier to minimize irradiation does to healthy tissue, by confining the field, controlling the energy and limiting the dose. For an illustrative skin treatment, system 10 can effectively treat the dermis while sparing the epidermis. Additionally, system 10 can be used to treat the anastomosis of blood vessels such as the femoral artery, popliteal artery and carotid artery during surgery in order to prevent restenosis while minimizing irradiation of surrounding tissues. Another benefit is that system 10 can irradiate the microvasculature of the surgical bed to reduce the probability of surgical adhesions.

Figure 2:
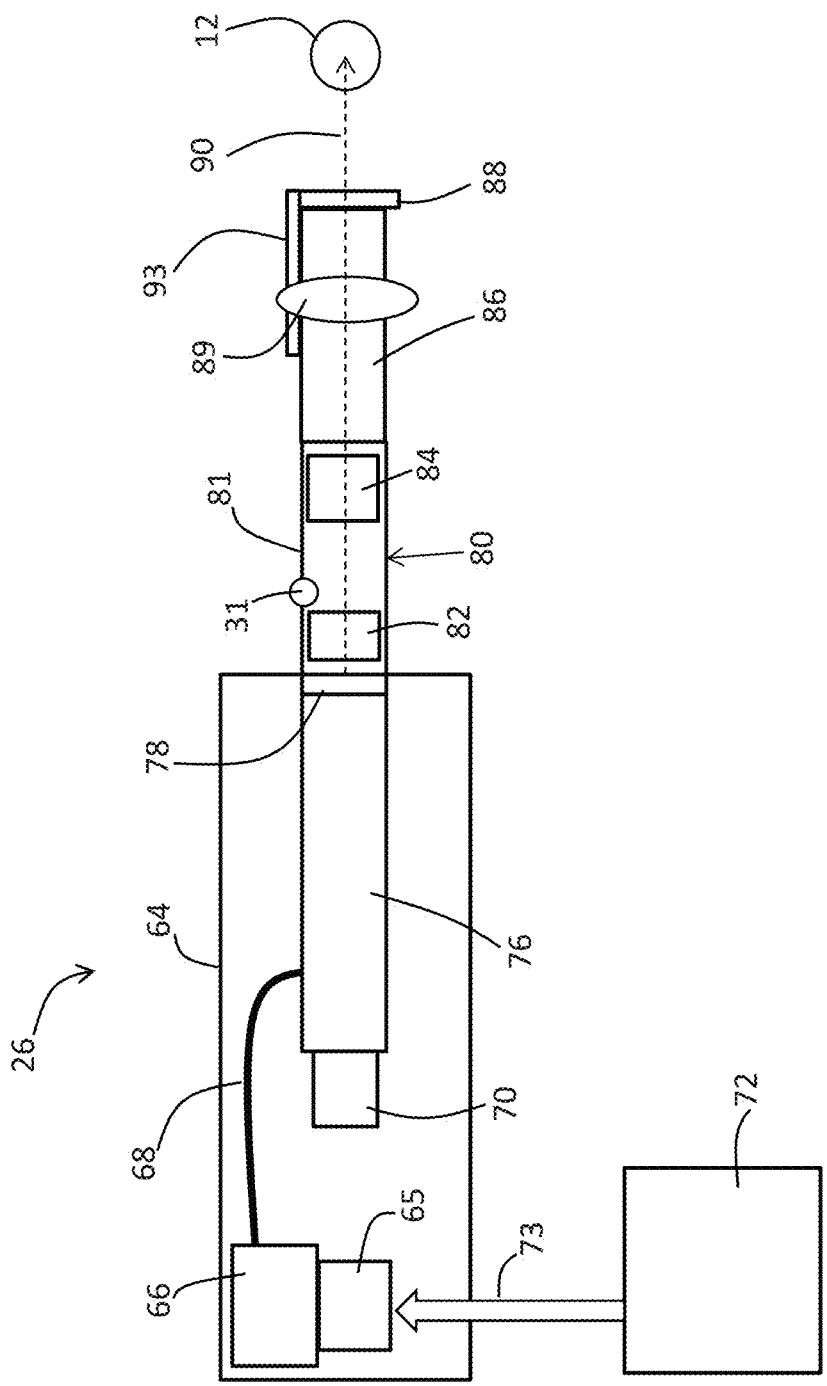
FIG. 2 schematically shows more details of an illustrative electron beam generation unit used in the electron beam radiation system of FIG. 1.

Exemplary features of one embodiment of a suitable electron beam generation unit 26 useful in system 10 are shown schematically in FIG. 2. As seen in FIG. 2, electron beam generation unit 26 generally includes housing 64 that contains a modulator 65, microwave source 66, a microwave network 68, an electron source 70, a linear accelerator 76, a collimator 80, an applicator 86, and a field defining shield 88. An external power supply 72 supplies power to the modulator 65 via power cable 73. Power supply 72 and power cable 73 as an option may be included inside housing 64 along with other components. An exit window 78 is provided at the interface between linear accelerator 76 and collimator 80. Scattering foil system 82 and ion chamber 84 are housed in collimator 80. Unit 26 generates an electron beam, which is aimed along substantially linear electron beam path 90 from accelerator 76 straight through applicator 86 to the target site 12 (shown in FIG. 1). An optional field defining shield 88 is placed at the exit of the applicator 86. A first sensor 31 is deployed with respect to collimator 80 for use in the feedback control strategy described further below. In such embodiments, ion chamber 84 among other functions also may serve as a second sensor in the feedback control strategy.

Electron beam generation unit 26 as shown in FIG. 2 is the type that uses linear acceleration techniques to boost electron beam energy to desired levels. The use of linear accelerator structures to generate electron beams for therapeutic uses is well known. Additionally, electron beam generation unit 26 is a "straight through" type of system. As known in the art, a straight through system aims an electron beam at a target site along a generally linear path from the exit window 78 of the linear accelerator 76 straight through to the target site 12. This helps to ensure use of much of the beam current produced. Bending systems, in contrast, waste greater proportions of the beam current through absorption in bending magnet slits. Wastage of beam current in bending systems generally produces substantially greater background radiation per unit of dose delivered. A linear, straight-through beam line minimizes such beam loss and better optimizes dose per unit current to the target site. This means that the linear systems need less shielding. Straight through systems, therefore, tend to be smaller, more lightweight, and more compact than alternative systems that use heavy magnets and heavy shielding to aim electron beams on bent paths to a target site. An additional advantage of a straight through system is that energy may be varied quickly as there is no eddy current diffusion time limit or hysteresis as with bent beam systems. This makes linear, straight through systems more suitable for intraoperative procedures.

One example of such a system suitable for intraoperative procedures is described in U.S. Pat. No. 8,269,197 assigned to IntraOp Medical Corporation. Another example of such a system suitable for intraoperative procedures is the electron beam machine commercially available from intraOp Medical Corporation under the trade designation MOBETRON. Generally, linear, straight through systems such as these are a result of engineering a compact linear accelerator that can fit when vertical under ceiling heights common to many procedure sites such as treatment rooms or surgery rooms. These compact systems avoid complex bending systems that tend to generate spurious background radiation that necessitates massive shielding.

As a key advantage in the practice of the present invention, such straight-through systems are able to respond more rapidly and precisely to the feedback control strategies of the present invention discussed further below. The feedback strategies of the present invention can be implemented into new electron beam machines. Alternatively, these strategies can be easily retrofit into existing machines such as the MOBETRON branded machines or the machines described in U.S. Pat. No. 8,269,197.

Still referring to FIG. 2, modulator 65 receives power from the power output of power supply 72 via cable 73. Power supply 72 may be any suitable source of electricity. Power supply 72, as an option, may be a component of a continuous source of electricity from a power utility. Alternatively, power supply 72 may be battery powered, permitting untethered operation of electron beam generation unit 26. Modulator 65 accepts the power from power supply 72 (which may be line power, battery power or any suitable power source), and converts it to short pulses of high voltage that it applies to the microwave source 66. Microwave source 66 converts the voltage into microwave or RF energy.

Examples of suitable microwave sources for use as microwave source 66 include a magnetron or a klystron to power linear accelerator 76. A magnetron is more preferred as being less expensive and simpler to incorporate into system 10.

Many suitable embodiments of a magnetron operate using X-band, S-band, or C-band frequencies. X-band devices are more preferred, as other embodiments of unit 26 tend to be heavier when using S or C band devices. X-band frequency technology also tends to minimize the diameter, and hence the weight, of the accelerator structure. One illustrative example of a suitable magnetron operating at X-band frequencies is the Model L-6170-03 sold by L3 Electron Devices. This magnetron is capable of operating at a peak power of about 2.0 megawatts and 200 watts of average power.

Microwave network 68 conveys the microwave or RF power from the microwave source 66 to the linear accelerator 76. The microwave network 68 often typically includes a waveguide (not shown), circulator (not shown), a load (not shown), and an automatic frequency control system (not shown). The use of these components in an accelerator system is well known to those skilled in the art and has been described in the patent literature. See, e.g., U.S. Pat. No. 3,820,035. Briefly, microwaves from the RF source passes through the circulator before entering the accelerator guide to protect the RF source from reflected power from the accelerator 76. Instead, the power not absorbed in the accelerator 76 is reflected back into the circulator and shunted into a water-cooled or air-cooled dummy load. In the preferred embodiment, air-cooling is preferred as air cooling reduces weight and minimizes servicing issues. An AFC circuit is used to keep the resonant circuit tuned to the microwave frequency. Air cooling works in the practice of the present invention because magnetron average power, e.g., 200 W in an illustrative embodiment, is relatively low for electron beams. In contrast, x-ray machines typically involve average power in the range from 1 kW to 3 kW. The ability to use air cooling with electron beams is one factor that helps preferred electron beam machines of the present invention to be so compact and lightweight.

Microwave or RF power may be injected into the accelerator structure through a fixed waveguide if the microwave source 66 (e.g. a magnetron) is mounted on a rigid assembly (not shown) with the linear accelerator 76. Alternatively, a flexible waveguide may be used in the microwave network 68. As one option for implementing the feedback principles of the present invention, microwave or RF power supplied to the linear accelerator 76 through microwave network 68 may be modulated in the case of a magnetron by varying the pulsed high voltage supplied to the magnetron from power supply 72. Modulating the voltage of the power supply 72 in this manner allows the energy level, and hence penetration depth, of the electron beam 16 to be controlled and adjusted to many different desired settings with excellent precision using the feedback strategies of the present invention. For a klystron, the same approach may be used. Alternatively, the input microwave power to the klystron may be varied.

In parallel with microwave source 66 supplying microwave or RF energy to linear accelerator 76, electron source 70 supplies electrons to linear accelerator 76. Electron source 70 typically includes an electron gun and features that couple the gun to the linear accelerator 76. Many different embodiments of electron guns are known and would be suitable. For example, some embodiments use a diode-type or triode-type electron gun, with a high-voltage applied between cathode and anode. Many commercially available electron guns operate at voltage ranges between 10 kV to 17 kV, though electron guns operating at other voltages may, in some embodiments, also be used. The voltage often is either DC or pulsed. In the case of the triode-type gun, a lower grid voltage also is applied between the cathode and grid. The grid can disable or enable the beam, and the grid voltage may be varied continuously to inject more or less gun current. The grid voltage may optionally be controlled through a feedback system. A skilled worker in the field of linear accelerator engineering is able to understand and choose an appropriate gun design suitable for the linear accelerator 76 to be used.

One example of a commercially available electron gun suitable in the practice of the present invention has been sold by L3 Electron Devices (formerly Litton) under the product designation M592 Electron Gun. The injector cathode of this particular gun operates in some embodiments at 10 to 14 kV and has a very small diameter emitting surface. This design is intended to provide low emittance and good capture efficiency while maintaining low energy spread. Typical pulse widths for operation may be in the range from 0.5 to 6 microseconds.

The RF source is pulsed by a modulator 65. It is preferred that the modulator 65 be solid state based rather than tube based to reduce weight and improve portability. The pulse repetition frequency (PRF) may vary from about 20 to about 240 pulses per second and the pulse width from about 2 to 4 microseconds. The combination of PRF and pulse width is one factor that impacts the dose rate of the emerging electron beam. For diode-gun systems, the gun likewise may be pulsed by the same modulator system, albeit with an intervening gun transformer to permit a step in voltage.

Linear accelerator 76 is configured to receive the microwave or RF power from the microwave network 68. Linear accelerator 76 also is configured to receive the electrons from the electron source 70. Linear accelerator 76 is coupled to the microwave network 68 and the electron source 70 in a manner effective to use the microwave or RF power to accelerate the electrons to provide electron beam 16 having an energy in the desired operating range, e.g., from 0.1 MeV to 6 MeV, preferably 0.2 MeV to 5 MeV, more preferably 0.3 MeV to 4 MeV. And even more preferably 0.5 MeV to 2 MeV.

A variety of different linear accelerator structures would be suitable in the practice of the present invention. For example, linear accelerator 76 may have a structure that implements any of a variety of different cavity coupling strategies. Examples of suitable structures include those that provide side cavity coupling, slot coupling, and center hole coupling. C. J. Karzmark, Craig S. Nunan and Eiji Tanabe, Medical Electron Accelerators McGraw-Hill, New York, 1993). Linear accelerator 76 also may have a structure that implements a variety of different symmetry strategies. Examples of suitable structures include those that provide periodic, bi-periodic, or tri-periodic symmetry. Examples of suitable accelerator structures also may implement a range of standing wave or travelling wave strategies. Examples of suitable linear accelerators 76 also may be selected to operate with many different bands of microwave or RF power. Examples of suitable power bands include S-Band (2-4 GHz), C-Band (4-8 (GHz), X-Band (8-12 GHz), and still higher frequencies. David H. Whittum, "Microwave Electron Linacs for Oncology", Reviews of Accelerator Science and Technology, Vol. 2 (2009) 63-92. In some illustrative embodiments, the linear accelerator 76 uses a low profile structure design, incorporating on-axis hi-periodic cavities operated at X-band frequencies. U.S. Pat. No. 8,111,025 provides more details on charged particle accelerators, radiation sources, systems, and methods, Side-coupled X-band accelerators and on-axis and side-coupled S-hand and C-band accelerators are other suitable examples.

The linear accelerator 76, its attached electron source 70, and one or more other components of electron beam generation unit 26 may be mounted inside housing 64 on a strongback (not shown) or other suitable support member. The linear accelerator 76 and electron source 70 may be encased in lead or other shielding material (not shown) as desired to minimize radiation leakage. The higher the resonant frequency of the accelerator guide, the smaller is the diameter of the structure. This results in a lighter-weight encasement to limit leakage radiation. An advantage of linear, straight through machines is that the shielding requirements are less severe than machines that using beam bending strategies. This allows straight-through electron beam radiation machines to be deployed for intraoperative procedures rather than being deployed in remote locations inside heavily shielded rooms.

During operation, the network, the linear accelerator and the microwave source 66 experience heating. It is desirable to cool unit 26 (particularly the units 65, 66, the circulator and loads in 68, and 76) in order to dissipate this heat. A variety of strategies can be used to accomplish cooling. For example, accelerator structure 76 and microwave source 66 can be water-cooled as is well known. In addition, the practice of the present invention permits operation at low-duty cycle, for which air-cooling would be quite adequate. The ability to practice air cooling simplifies the construction of unit 26 and helps to make the unit 26 smaller and more compact. The result is that the corresponding system 10 (See FIG. 1) is easier to deploy and use in intraoperative procedures.

An exit window 78 at the beam outlet of linear accelerator 76 is to help maintain a vacuum within the accelerator. The window 78 should be strong enough to withstand the pressure difference between the accelerator vacuum and the ambient atmospheric pressure, e.g., a difference of about 15 psi in some instances, but should be thin enough to avoid excessive beam interception and/or bremsstrahlung production. Balancing these factors, the window 78 may be formed of titanium in many embodiments. Alternatively, beryllium or other metallic or composite materials also may be used.

The accelerated electron beam 16 exits the linear accelerator 26 through exit window 78 and next continues on a linear path through collimator assembly 80 that receives, broadens, and flattens the beam. To implement feedback strategies of the present invention, one or more sensors may be deployed in or around collimator 80 in order to detect two or more independent characteristics of the beam. In the illustrative embodiment of FIG. 2, sensor 31 functions as a first sensor, and ion chamber 84, among its other functions, functions as a second sensor. Sensor 31 schematically is shown to the side of collimator 80, and thus generally out of the beam path in this embodiment. Other deployments, including deployments in the beam path or other locations downstream from exit window 78 may be used, if desired. The feedback strategy of the present invention is described further below with respect to these and other sensor configurations.

Collimator 80 can include a housing 81. Housing 81 may be constructed of materials that help contain bremsstrahlung radiation, or the collimator design itself could be sufficient to contain the bremsstrahlung radiation. Inside housing 81, scattering foil system 82 and ion chamber 84 are provided. Scattering foil system 82 serves multiple functions. For example, electron beam systems typically produce beams of small transverse dimension, on the order of 1 mm to 3 mm across, much smaller than typical treatment fields. Scattering foil system 82 helps to broaden the electron beam 16. The scattering foil system 82 also helps to flatten electron beam 16. In many modes of practice, the beam passes through the scattering foil system 82 to help in shaping of the isodose curves at the treatment plane at target site 12.

In illustrative modes of practice, scattering foil system 82 helps to enlarge the accelerated beam 16 from being several square millimeters in cross section to several square centimeters in cross section. Uniformity of dose across the treatment field is a desired goal to simplify dose planning for therapeutic applications. For example, collimator 80 with or without applicator 86 may function to provide a flat electron beam dose profile such that the coefficient of variation of the beam dose across the full width at half-maximum (FWHM) of the beam is less than ±50%, less than ±40%, less that ±30%, less than ±20%, less than ±10%, less than ±5%, less than ±2.5%, or less than ±1%. Those of skill in the art will recognize that the coefficient of variation of the electron beam energy across the FWHM may have any value within this range, for example, about ±5%. In some embodiments, the collimator may function to broaden the electron beam to field sizes that are 1 cm to 25 cm across.

A typical scattering foil system 82 includes at least one, even two or more, and even three or more scattering foils (not shown). The distance between the two or more foils can vary, depending on the energy range of the unit, the field size needed for the treatment application, and the geometry and materials of the mass elements in the treatment head. Generally, electron scattering foils may be designed using techniques such as empirical design iteration or Monte Carlo simulations. Other means of providing uniformity could rely on magnetic phenomena. For example, steering coils could be employed to raster the beam across a programmed area. Alternatively, a quadrupole magnet system could be used to modify the beam size at the target plane.

Ion chamber 84 serves multiple functions. In one aspect, ion chamber 84 monitors the radiation dose delivered by the system and radiation when the prescribed pre-set dose is delivered. The monitor features of ion chamber 84 may be segmented transversely to provide a reading of beam position in the transverse plane. This reading may be used in a conventional feedback control system to provide current to steering coils upstream, so as to steer the beam and continuously correct any beam offset or symmetry error. Advantageously, in the practice of the present invention, this reading may be used in an innovative feedback control system (described further below) used to control the electron beam energy, and hence penetration depth at the target site, with excellent precision. As another function, ion chamber 84 may be used to terminate the beam and limit the amount of radiation received at the target site if an issue with the electron beam is detected. For example, a loss of a scattering foil could result in delivery of an excessive dose. In this fashion, ion chamber 80 and associated electronics provide protective interlocks to shut down the beam under such circumstances.

An optional applicator 86 is positioned proximal to the exit end of collimator 80. In some modes of practice, applicator 86 may be held in a desired position by separate separating structure that holds applicator 86 in alignment with collimator 80. In other modes of practice, applicator 86 may be coupled to collimator 80. However, in instances of such coupling, if the applicator is metallic and could come into contact with the target site, the applicator 86 desirably is electrically isolated from collimator 80 and the rest of system 10. This can be accomplished in various ways such as by interposing an insulative coupling between applicator 86 and collimator 80 or between applicator 86 and patient 14, or by forming applicator from a material that is inherently insulating (e.g., polymethyl(meth)acrylate often referred to as PMMA, quartz, ceramic, or the like). It may be desirable to minimize, and more preferably to avoid, a gap between the collimator 80 and applicator 86 to eliminate or reduce stray electrons that could be scattered through the gap that could result in undue stray radiation in the ambient room. However, at lower electron beam energies used in many modes of practice, this is less of a concern with the present invention as compared to conventional practices that use higher electron beam energy levels at the target site.

The accelerated and collimated electron beam is aimed at a target site 12 through applicator 86. The applicator 86 is configured so that the electron beam continues on linear electron beam path 90 straight through to the target site 12. In many modes of practice, the applicator 86 further helps to define the shape and flatness of the electron beam 16. Applicator 86 also makes it easier to aim the electron beam while minimizing the manipulation of, contact with, or disturbance of the patient or target site. Furthermore, the use of applicator 86 helps to avoid stray radiation and minimizes the dose delivered to healthy tissue by confining the radiation field.

Applicator 86 may include components to help further modify the electron beam 16 depth-dose (energy) or flatness. For example, energy reduction with low bremsstrahlung can be achieved by interspersing thin (0.5-1 mm) sheets of plastic or sheets made from low atomic number material into the applicator 86 in a slot provided to accept them. Materials with higher electron density also may be used and could be thinner for the same absorption. The applicator could also incorporate element(s) to act as a secondary scattering component. These may be made from suitable shaped low atomic number materials that help to further scatter electrons within the volume of applicator 86. Examples of such materials, but by no means exclusive to these materials, include aluminum, carbon, and copper and combinations of these. These can be located in applicator 86 at positions determined by Monte Carlo calculations or empirically for the energy and field size needed for the application.

In some modes of practice, a transparent or partially transparent applicator 86 may be beneficial. For example, such an applicator design may allow easier viewing of the treatment site. Applicators fabricated at least in part from PMMA, quartz, or the like would permit such viewing.

Unit 26 may be positioned in any orientation or position with respect to the target site regardless of patient orientation. In many modes of practice, the distance from the exit end of the applicator 86 (or the end of field defining shield 88, discussed below) to the surface of the target site can vary from contact with the target site to distances up to about 10 cm from the patient surface. The distance can be determined by any suitable measurement technique such as by either mechanical measurement or an electronic rangefinder. In some embodiments, the system and/or applicator may be positioned manually to achieve any orientation or position relative to the target. In some embodiments, system and/or the applicator may be positioned using one or more motor drives for automated control of orientation and position. For example, the applicator 86 could be placed by hand and held in place by a suitable support structure (not shown). Then the electron beam machine would be docked (i.e., aligned) to the applicator 86. The applicator 86 desirably is electrically isolated from other components of system 10, particularly in treatments in which the applicator contacts or is close to the patient 14.

The applicator 86 may have a variety of shapes, such as being shaped to produce circular, square, irregular, or rectangular fields on the target site. One example of an applicator design, called a scan horn, creates long narrow fields by having scattering elements within the applicator that scatter electrons preferentially along the length of the field. In some embodiments, the scan horn may be used to confine the irradiated area to a strip of from about 2 cm to about 10 cm in length, and about 0.2 cm to about 1 cm in width.

Figure 3:
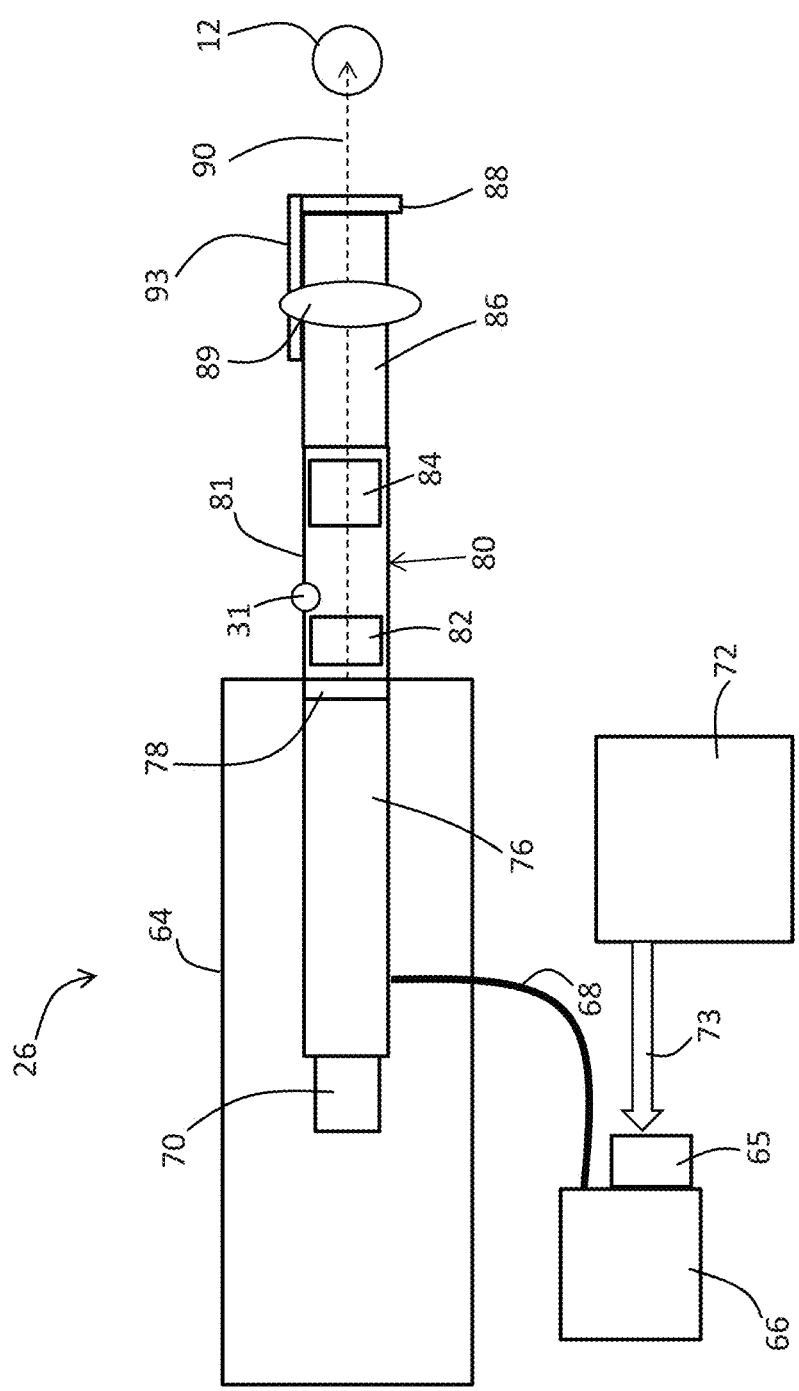
FIG. 3 schematically shows an alternative embodiment of an electron beam generation unit useful in the electron beam radiation system of FIG. 1.

FIG. 3 shows an alternative embodiment of the electron beam generation unit 26. The embodiment of FIG. 3 is identical to the embodiment of FIG. 2 except that the microwave source 66 and a portion of the microwave network 68 are external to housing 64. Rotational motion between the two ends of the network 68 can be practices by incorporating one or more rotary joints into network 68 according to conventional practices.

FIGS. 2 and 3 show how an absorber 89 may be mounted on applicator 86 in a manner effective to tune the electron beam to achieve the desired penetration depth. By having a library of absorbers 89 with fine, stepwise differences in electron beam absorption, different penetration depths in fine increments can be delivered to treatment sites such as site 12. In the meantime, the feedback strategies of the present invention (described further below) are used to stabilize the electron beam with high precision prior to timing by the absorber 89. To change to another penetration depth setting, one or more different absorbers 89 are presented to the beam and/or the machine may be set to produce an electron beam with a different energy level that is presented to the one or more absorbers 89. The different absorbers 89 may be installed manually or via automation.

FIGS. 2 and 3 show absorber 89 being mounted to applicator 86. The absorbers 89 may be located in other positions and still provide effective tuning. Generally, the absorber 89 is deployed in the path 90 of the electron beam between the exit window 78 and the target site 12. Many suitable embodiments of absorber 89 are fabricated from one or more low Z materials above atomic number 4. Exemplary materials useful to form absorber 89 include carbon, aluminum, beryllium, and combinations of two or more of these. Higher Z materials could be used, but with the risk of generating undo amounts of Bremsstrahlung radiation.

FIGS. 2 and 3 also show machine vision capability integrated with applicator 86. In these embodiments, machine vision is achieved by mounting one or more endoscopes 93 onto applicator 86. Endoscope 93 allows real time video imaging of target site 12. Endoscope 93 or other machine vision capability is helpful to allow target site 12 to be viewed without obstruction by applicator 86, shield 88, or other components of system 10. As one advantage, endoscope allows real time viewing of target site 12 as system 10 is set up and aimed at the target site 12. This can be helpful to make sure that system 10 is aimed properly at site 12 without undue misalignment or tilting. An operator can also view the captured image information to observe the site 12 during a treatment. This will allow the operator to capture image information to document the treatment. Also, the operator can observe to make sure that the patient 14 does not move out of the proper set up as a treatment proceeds. An endoscope is very suitable for this, as endoscopes are flexible for easy mounting, capture high quality, real time images, and are inexpensive.

FIGS. 2 and 3 show embodiments of unit 26 in which collimator 80 and applicator 86 are separate components. In some embodiments, functions of collimator 80 and the applicator 86 may be integrated into a single component in the form of a collimator (not shown) including primary and secondary collimator sections. In this embodiment, the primary collimator contains the scattering foils and ion chamber. The secondary collimator may be used to restrict the emerging electron beam to circular or oblong shapes of varying diameters or to rectangular shapes of varying lengths and widths, with widths as small as 5 mm, and a length equal to the length of the maximum rectangle that can be circumscribed in the maximum inner circular diameter of the collimator. For example, if the maximum inner circular diameter of the collimator were to be 5 cm, for a rectangle that was 1 cm wide, the maximum length would be 4.9 cm. Any of the lower and upper values described in this paragraph may be combined to form a range included within the disclosure, such that the expanded electron beam diameter may be from about 5 mm to about 5 cm. Those of skill in the art will recognize that the expanded electron beam diameter may have any value within this range. Larger radiation fields may be achieved by extending the length of the collimator and/or using additional scattering from specially designed applicators that attach to the collimator Referring again to FIG. 1, unit 26 is aimed so that electron beam 16 contacts and irradiates target volume 18 on patient 14 to a desired penetration depth. The linear acceleration and optional straight through characteristics of electron beam 16 allow the beam 16 to be rapidly responsive to feedback control to allow the penetration depth to be adjusted to any desired penetration depth either continuously over the operating range of energies or in small increments corresponding to penetration depth adjustments of 3 mm or less, preferably 2 mm or less, more preferably 1 mm or less. Additionally, setting a selected penetration depth with a precision within +/−1 mm or even better would be achieved in illustrative modes of practice. Because energy level of the electron beam 16 and penetration depth are highly correlated, this means that controlling the energy level provides excellent control of the desired penetration depth.

Being able to control and adjust penetration depth with such excellent precision is advantageous in many procedures. As one example, using system 10 for treatment of the dermis while sparing the epidermis would require such precision because the dermis is such a thin tissue. Due to the depth sensitive nature of the configuration of the epidermis to the dermis, and other structures for other applications, having a depth and adjustment precision of 1 mm or better is very advantageous. In general, the thickness of the epidermis varies from patient to patient as well as among different sites on a given patient. Thus, a treatment may involve first obtaining an indication of epidermal thickness in the course of performing a surgical procedure. If a practitioner such as a surgeon or therapist should determine that the epidermal thickness is, for example, 3 mm, system 10 allows the practitioner to quickly provide radiation of the appropriate depth-dose characteristic on the spot. System 10 addresses deficiencies of conventional methods and devices by allowing this rapid, precise control and adjustment of the electron beam to meet patient needs.

Still referring to FIG. 1, system 10 includes feedback control system 28 configured to permit controlling and adjusting the penetration depth provided by electron beam 16 with improved precision and stability. Advantageously, control system 28 uses an innovative feedback strategy that allows rapid, real-time control and adjustment of the electron beam energy to keep the beam stable or to adjust the beam in continuous or small increments as desired to achieve desired energy settings and corresponding penetration depths. Control system 28 is easily implemented and provides excellent, rapid feedback control of the electron beam energy, and hence of the penetration depth at the target site 12. Rapid feedback in illustrative embodiments may occur pulse by pulse. e.g., 60 Hz in typical modes of practice.

The precision of control system 28 for implementing, feedback control is excellent. For example, as discussed above, For example, setting the penetration depth with a precision within +/−1 mm or even better would be achieved in illustrative modes of practice. Moreover, the energy level, and hence penetration depth are rapidly responsive to feedback control to allow the penetration depth to be rapidly adjusted to any other desired penetration depth either continuously over the operating range of energies or in small increments corresponding to penetration depth adjustments of 3 mm or less, preferably 2 mm or less, more preferably 1 mm or less. This allows real time adjustment of the penetration depth, e.g., to quickly change from one penetration depth setting to another in the course of intraoperative radiation therapy.

Precision control of penetration depth requires a very stable electron beam radiation system. The feedback control system 28 of the present invention helps to ensure the beam energy remains stable when tuned to a particular setting. The feedback control system 28 also provides excellent resolution for controlling electron beam energy, and hence penetration depth, that is significantly improved beyond conventional practice for either bent-beam or straight-ahead beam machines. In providing such improved precision, control system 28, in practical effect, provides an energy servo for straight-ahead electrons. This is something that does not presently exist in commercially available straight through, linearly accelerated electron beam machines used for electron beam therapies.

Conventionally, it has been challenging to monitor an electron beam to achieve feedback control with this level of precision. One challenge is that it is difficult to monitor the energy of the electron beam energy directly. Placing suitable sensors in the path of the beam can unduly obstruct the beam. This can generate an undesirable level of x-rays, requiring additional shielding that undermines easy deployment in intraoperative sites. Another challenge is that measuring an individual characteristic such as current or the like instead of the energy level is easier, but unfortunately provides insufficient information on its own to apply feedback control of the energy level with excellent precision.

As shown in FIG. 1, control system includes at least one monitoring sensor that is used to detect at least two different characteristics of the electron beam. Monitoring in this embodiment includes at least two sensors in the form of first sensor 31 and a separate second sensor 34. In other embodiments, more sensors may be included. Alternatively, multiple sensor capabilities may be incorporated into a single sensor component. First sensor 31 measures a first characteristic (s1) of the electron beam 16. First sensor 31 sends a corresponding first sensor signal 32 to controller 38. Signal 32 corresponds to the value of the characteristic s1 measured by first sensor 31. Second sensor 34 measures a second characteristic s2 of the electron beam 16. Second sensor 34 sends a corresponding second sensor signal 36 to controller 38.

Controller 38 then derives an analog characteristic, A, of electron beam energy from the detected characteristics s1 and s2 presented by the signals 32 and 36. To accomplish this, controller 38 receives the first and second sensor signals 32 and 36 and uses one or more suitable functions. A=F(s1, s2), in order to derive the analog characteristic, A. The analog, from one perspective, is a synthetically derived, composite characteristic of the electron beam. Unlike a single natural characteristic of the beam, such as s1 or s2 alone, the analog characteristic show high correlation to the energy level with excellent resolution. That is, relatively small, detectable changes in the analog composite correspond to measurable and controllable small increments of energy level. The result is that measuring at least two different characteristics of the beam and using those to derive the analog characteristic allows the energy level to be easily controlled by control system 28 with high precision.

Examples of electron beam induced signals that can be measured and used to derive the analog characteristic include current from a toroid through which the beam passes, ion-chamber current, current from an insulated foil or filter, diode detector current, signal from an antenna not electrically isolated from the beam, signal from a cavity excited by the beam, scintillator. Some of these signals may be used more than one time to derive suitable, different information from which the analog can be derived. One example of this would be a toroid signal before and one after a flattening filter. Together, the two different toroid signals provide current figures dependent on secondary backscatter, an energy dependent quantity. Another example of this would be presenting two different radiation detectors to the electron beam, wherein the absorbers incorporated into the detectors have different thicknesses, respectively. The detectors do not have to be co-located. For some characteristics, it may be desirable to measure the characteristic several times in a given time interval, and then use an average, mean, or other similar value in the analog function.

The function used to derive the analog characteristic is generally any function of the sensed characteristics that provides unique function values over the interval ranges of both sensed characteristics within the operating energy range of system 10. The contributions of the characteristics to the value of the function should be non-negligible. The contributions are non-negligible for a set of sensed characteristics if the value of the function changes by more than 1% when the $R_{80}$ penetration depth of the electron beam changes by 1.0 mm. Suitable functions also provide function values with excellent resolution for tuning the energy. In other words, changes in the measured characteristics correspond to controllable energy differences sufficient to achieve the desired precision specifications described herein. In general, noise could limit resolution. A wide variety of conventional techniques to reduce noise in data acquisition on beamline pickups may be helpful to reduce the impact of noise, including shielded cable, guard electrodes, filtering, gating, lock-in amplifier, and/or the like.

As one example, a simple ratio of the sensed characteristics is generally an excellent choice for a function that is used to derive the analog characteristic. Ratio functions also tend to provide excellent resolution for setting and tuning the energy level of the beam. Other functions also would be suitable. Examples of other simple, suitable functions include functions that sum, calculate the difference, and/or calculate the product of the sensed characteristics. If the sensed characteristics are quite different by 2 or more orders of magnitude, it may be desirable to use a natural or log 10 value of the characteristic with greater numerical magnitude. Alternatively, coefficients or powers may be used so that the general contributions of each characteristic to the value of the analog function are more similar.

Because the derived analog characteristic correlates strongly with the energy level of the electron beam 16, the electron beam energy corresponding to the derived analog characteristic can be determined from the correlation. If the analog characteristic and/or corresponding electron beam energy are different than a desired reference analog value or electron beam energy, controller 38 generates a control signal 40 to control and/or adjust the electron beam energy or to turn off the beam pursuant to an interlock protocol. For example, controller 38 can generate an error signal that is derived from the analog characteristic and a corresponding reference value. Controller 38 can then use the error signal to generate control signal 40. The feedback control strategy allows the electron beam energy to be shut off pursuant to an interlock protocol or controlled/adjusted at a desired setting in the system operating range, e.g., in the range suitable to provide the desired penetration depth, usually occurring in an energy range at the target site of 0.1 MeV to 6 MeV. The energy setting may be selected to correspond to a desired penetration depth of the electron beam irradiation at the target site 12. By deriving the control signal 40 from the analog characteristic, control system 28 is able to set, control, and adjust the electron beam energy with excellent precision. Advantageously, electron beam 16 is able to respond rapidly to control signals so that the feedback control can be implemented in real time.

Controller 38 can use the control signal 40 in different ways to implement such feedback control. As one example, control signal 40 can be used to shut off the electron beam pursuant to an interlock protocol. As another example, control signal 40 can be used to adjust power source(s) that generate the electron beam in order to tune electron beam energy as desired. In some embodiments, such power-based control can be implemented by feedback control of the microwave source 66 (See FIG. 2 or 3) and/or the electron source 70 (See FIG. 2 or 3). Using the feedback control strategies of the present invention, modulator or magnetron-based feedback (e.g., feedback to regulate modulator output voltage or magnetron frequency) allows adjusting electron beam energy in steps or continuously over the desired operating range, e.g., 0.1 MeV to 6.0 MeV. For example, the modulator output voltage can be regulated to affect current supplied to the magnetron and the microwave power. The magnetron frequency may be regulated, which impacts the amount of power delivered to the accelerator 86 (FIGS. 2 and 3). In addition to these strategies or as an alternative to these strategies, feedback control strategies may be used with respect to other system features that are used to establish the electron beam, including gun voltage or the like. The gun voltage can be regulated to impact the launch velocity of electrons, phasing, capture, and energy spectrum.

As another approach to implement feedback control, control signal 40 can be used to adjust the settings of one or more physical system components, e.g, one or more electron beam absorbers, whose selected position setting can be used to modulate the electron beam energy. One such adjustable component is an electron beam absorber of variable thickness that can be adjusted to present different thicknesses, and hence different absorptions, to the electron beam. Such absorber-based control may be accomplished with single absorbing plates providing a range of selectable thicknesses, a variable thickness ribbon, or a rotating body containing whose degree of rotation presents variable thickness absorption to the electron beam. Using the feedback control strategies of the present invention, absorber-based feedback allows adjusting electron beam energy in steps or continuously over the desired operating range, e.g., 0.5 MeV to 6.0 MeV.

When using any absorber(s) to help tune the electron beam, control system 28 desirably includes monitors that confirm that an absorber is in the correct installed position. If the monitors provide a signal indicating that the position is incorrect, an interlock protocol is triggered that prevents the electron beam from being turned on. Similarly, in those embodiments in which system 10 includes a plurality of absorbers with different thicknesses, a particular absorber or combination of absorbers is the proper absorber selection for carrying out a particular treatment at a desired penetration depth. Accordingly, control system 28 desirable contains monitors that check if the installed absorber matches the machine settings for the particular treatment. If the improper absorber is installed for the selected procedure, an interlock protocol is triggered that prevents the beam from turning on. As a further safety function, a particular treatment will usually involve delivery of a particular radiation dose. Control system 28 desirably monitors the delivered dose in real-time and initiates an interlock protocol to turn off the electron beam to avoid overdose.

Some embodiments of the present invention combine both power-based and absorption-based feedback control of the electron beam energy, and hence penetration depth.

Figure 4:
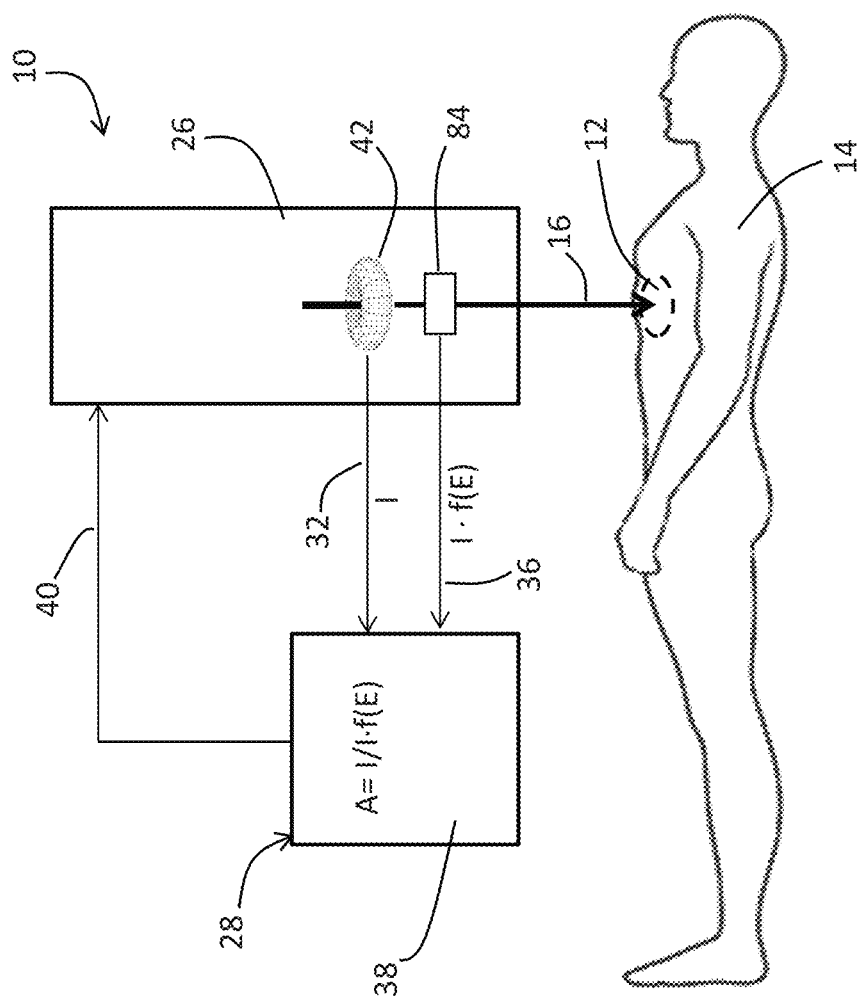
FIG. 4 schematically shows an illustrative embodiment of a feedback control system of the present invention used in the electron beam radiation system of FIG. 1.

FIG. 4 shows a preferred embodiment of control system 28 for controlling electron beam 16 emitted by electron beam generation unit 26. In this embodiment, toroid 42 serves as a first sensor, while ion chamber 84 serves as a second sensor. The toroid 42 is deployed in a manner effective to monitor beam current incident on the ion chamber 84. The toroid 42 is an excellent sensor because electron beam 16 passes through the central, open aperture of toroid 42. In practical effect, the physical body of toroid 42 fits around the passing electron beam. This means that toroid 42 can sense current, I, without obstructing or otherwise physically blocking electron beam 16. In the case of using a toroid as a current sensor, the toroid senses the beam current passing through the toroid and produces a an output waveform such as V=kI, where k is a constant, e.g., 10 V/A as one example. Toroid 42 sends a first sensor signal 32 to controller 38 that indicates the measured current, I. Toroid 42 functions in this embodiment as a current monitor. Other monitors also can be used that detect characteristics that are functions of electron beam energy. Illustrative alternatives to toroid 42 include a dose monitor, a second ion chamber, a microwave cavity, a resistive wall current monitor, a stripline or button pickup on the beamline, or the like. Solid state sensors and scintillators also could be used as monitors for electron beam characteristics.

In the meantime, ion chamber 84 is used to detect beam-induced ionization, E. Ion chamber 84 sends a second sensor signal 36 to controller 38 that indicates the ion chamber current, which may be viewed as a current value that results from a product of two functions, I·f(E), where f(E) is a current function impacted by system factors that cause voltage fluctuations that influence the electron beam energy. Although individual values for each of I and f(E) might not be known as detected by the ion chamber, the ion chamber measures and provides a specific current value that depends on both functions. Advantageously, the present invention uses feedback strategies that derive an analog (described further above and below) whose fluctuation highly correlates to electron beam energy. Advantageously, deriving the analog allows feedback control to be practiced without ever actually knowing the precise function f(E), because its composite variation in the form of the analog can be accurately measured and reliably correlated with and calibrated to depth dose (such as by measurements with reference to dosimetry along the lines of the AAPM TG-51 Report) and thereby used by the feedback strategies. Other current functions (such as g(E) and h(E) discussed below) detected by ion chambers, radiation detectors, or the like are easily handled in a similar way by the feedback strategies of the present invention.

In addition to direct monitoring of dose rate through ionization chamber 84 in this manner for purposes of feedback control, other monitoring could be performed downstream to verify and document the dose delivered to the target site. Such other monitoring helps to verify that dose is limited to targeted structures. A straightforward approach for such other monitoring may involve one or more strategies such as making use of radiochromic film, Radiochromic Film Dosimetry, AAPM Report No. 63, (AAPM, College Park, 1998) optionally in conjunction with optically stimulated luminescence dosimeters. See, e.g., Caleb Price, Aaron Pederson, Chanté Frazier and John Duttenhaver, "In vivo dosimetry with optically stimulated dosimeters and RTQA2 radiochromic film for intraoperative radiotherapy of the breast," Med. Phys. 40, 091716 (2013).

Controller 38 uses the values for I and I·f(E) to generate an analog value, A that is derived from the function $A(I, I \cdot f(E)) = I \cdot f(E)/I$. That is, the ionization chamber current output, I·f(E), is divided by the beam current, I, or a suitable average of beam current I. The ratio I·f(E)/I is an analog value that has excellent correlation to electron beam energy even though I·f(E) or I individually do not provide a sufficiently strong correlation to provide the improved precision of the present invention. In effect, the ratio normalizes the energy-involved reading, making it more highly correlated to energy level. Otherwise, current fluctuation could make it difficult to monitor and/or control energy level with precision. The analog value of $A = I \cdot f(E)/I$ can then be used to derive an error value. One approach for doing this is to calculate a difference between the analog value and a reference analog value. In a preferred mode of practice, the ionization chamber can be configured to operate with a linear response. Non-linearity in the response can be accommodated by a variety of strategies, including the step of providing a suitable look up table based on I or I·f(E) readings, including using linear reference dosimetry.

In other words, the ion chamber 84 detects a current reading that is a product of two functions, namely current I and an energy function f(E). When the product function varies, it is difficult to assess from this product function alone if a variation is due to current or energy variation. Thus, the product function is weakly correlated to electron beam energy on its own, because of the contribution of the current factor. By separately measuring current and producing the analog given by the ratio of the two functions, fluctuations in the analog value are due to the variations in the function f(e). The result is that the analog computation is highly correlated to energy variation.

Based on the error, controller 38 can then apply conventional process control principles to implement a control signal 40 to turn off or tune the electron beam energy to the desired level. Control system 28 thus sets the energy level based on the closed loop signals detected from the electron beam. The actual control implemented may involve adjusting output voltage provided to the microwave source 66 by modulator 65, and hence the power output of microwave source 66. This in turn adjusts the frequency of the magnetron, or the electron gun voltage, in electron source 70, adjusting the position of an absorber with variable absorption, or combinations of these.

Thus, FIG. 4 shows feedback control system 28 as a precision energy servo in which a toroid 42 and an ion chamber 84 monitor different beam characteristics. In this mode of practice, the ratio of the currents from the two devices is compared to a reference value by processor 38 to generate the composite analog characteristic, an error signal, and corresponding control signal 40. The control signal 40 can be used by system 10 in different ways. For example, the control signal 40 can be used to implement an interlock protocol. Alternatively, the signal can be used to implement electronic control and adjustment of electron beam energy. As another option, the signal can be used to actuate components that modulate the electron beam.

Figure 5:
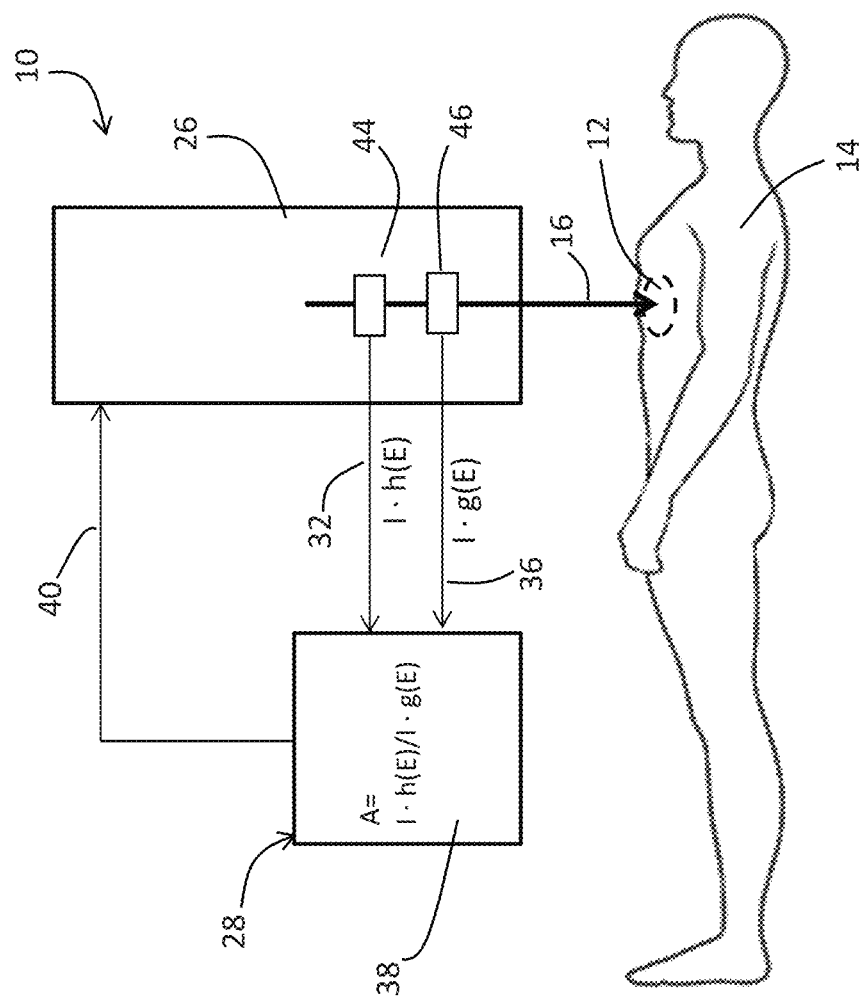
FIG. 5 schematically shows an alternative embodiment of a feedback control system of the present invention used in the electron beam radiation system of FIG. 1.

FIG. 5 shows an alternative embodiment of control system 28 for controlling electron beam 16 emitted by electron beam generation unit 26. Instead of using toroid 42 and ion chamber 84 as first and second sensors, control system 28 of FIG. 5 uses two radiation detectors 44 and 46 as the first and second sensors, respectively, each with different amounts of build-up and hence different response curves (adjusted, e.g., by including a different thickness of an absorber in front of each). The ratio of the two signals provides an analog indicator of beam energy that is similarly used for feedback and control of the beam energy. The detector 44 is deployed in a manner effective to monitor a first radiation dose, I·g(E). Detector 44 sends a first sensor signal 32 to controller 38 that indicates the measured radiation dose. In the meantime, detector 46 is used to detect a different dose rate, I·h(E). Detector 46 sends a second sensor signal 36 to controller 38 that indicates the measured radiation dose.

Controller 38 uses the values for I·g(E) and I·h(E) generate an analog value, A that is derived from the function $A(I, E) = I \cdot g(E)/I \cdot h(E)$. This ratio is an analog value that has excellent correlation to electron beam energy even though I·g(E) and I·h(E) individually do not provide a sufficiently strong correlation to provide the improved precision of the present invention. The analog value provided by this ratio can then be used to derive an error value. One approach for doing this is to calculate a difference between the analog value and a reference analog value.

Based on the error, controller 38 can then apply conventional process control principles to implement a control signal 40 to tune the electron beam energy to the desired level. Control system 28 thus sets the energy level based on the closed loop signals detected from the electron beam. The actual control implemented may involve adjusting the voltage of the power supply 72 and hence the power output of microwave source 66, adjusting the modulator current, adjusting the frequency of the magnetron, or the electron gun voltage, in electron source 70, adjusting the position of an absorber with variable absorption, or combinations of these.

Multiplate ion chambers also provide, in practical effect, at least two different detectors that can be used to derive an analog characteristic that correlates to electron beam energy. For example, an illustrative ion chamber may include two annular electrode pairs that are concentrically deployed around a passing electron beam. Due to the difference in radial displacement relative to the center axis of the passing beam, the ratio of the two detected currents would provide an analog that correlates to electron beam energy even though neither on its own provides the desired correlation due to the impact of current on the energy function.

One monitoring system of the present invention was tested that made use of use two ionization chambers in sequence as feedback sensors. These provided the desired monitor functionality shown in FIG. 5 (elements 44 and 46) when stacked one on the other. These were integrated into one dual-chamber transmission ion chamber installed in a collimator of a MOBETRON machine. The dual chamber device included two 0.001" thick foils of polyimid (Kapton) of diameter 65 mm captured between three 1.5 mm thick steel annuli with matching outer diameter, and inner diameter 45 mm. Prior to assembly, the foils were plated with 200 nm of Au with masking to define an active electrode area.

The active electrode area diameter is 40 mm for the upstream chamber electrode and is 15 mm for the downstream chamber electrode.

This dual-chamber component was installed in the collimator downstream from foils, mounted within the 7 cm collimator inner diameter. The first foil encountered by the beam is a 0.0006" Ti foil at the accelerator output, ("accelerator window") followed at a distance of 1.5 cm by a 0.001" Ta foil ("primary scattering foil"). After an additional 10-cm this is followed by a secondary scattering foil ("flattening filter"). The first ion chamber is located 2 cm further downstream, and the second ion chamber is located 0.5 cm after that Operating the MOBETRON machine at 12 MeV, each chamber independently provided a signal. The ratio of these two signals varied by 8% as magnetron current was varied by 16% in over 7 discrete steps. Depth dose was measured at each step and varied from 36 mm to 42 mm. This confirmed that the monitored features correlated to electron beam energy and penetration depth with excellent signal sensitivity.

Without wishing to be bound by theory, a rationale to explain the energy dependent mechanisms of the ion chamber response is provided. Radiation exposure in the ion chamber is produced by the beam, after interaction with other elements of the collimator geometry, including the chambers, together with secondary or subsequent emissions induced by the beam in this geometry. The larger electrode samples a wider portion of the beam profile than does the smaller electrode, and the wings of this distribution are more sensitive to beam energy, a feature of electron scattering. A second effect at work is that scatter and secondary emissions are enhanced by the presence of higher Z materials. The foils, the collimator, the steel rings and other materials provide an energy-dependent secondary source of radiation exposure to the ionization chambers. Thus, two mechanisms at work are energy dependence of the scattered angular distribution from the foils and energy dependence of secondary radiation.

The physical mechanisms and properties of scattering, including stopping power and mass scattering power, are well understood. Radiation Dosimetry: Electron Beams with Energies Between 1 and 50 MeV, International Commission on Radiation Units and Measurements, Report 35. Generally stopping power varies slowly with energy in the range of 0.5-2.0 MeV; however, angular scatter varies appreciably in this range. Among secondary sources of chamber ionization, radiative yield is low in the range of 0.5-2.0 MeV; however, backscatter is significant, especially for higher Z materials, and varies appreciably with energy. The phenomenon of electron backscatter has been described by Tatsuo Tabata, "Backscattering of Electrons from 3.2 to 14 MeV", Phys. Rev. 162 (2) October 1967 pp. 336-347. Kenneth F. Koral and Allan J. Cohen, Empirical Equations for Electron Backscattering Coefficients, NASA Technical Note, NASA TN D-2909.

Methods for design and implementation of scattering systems are known in the art. Bengt E. Bjarngard, et al., Electron scattering and collimation system for a 12-MeV linear accelerator, Med. Phys. Vol. 3, No. 3, May/June 1976 pp. 153-158. Sung-Joon Ye, et al., Monte Carlo techniques for scattering foil design and dosimetry in total skin irradiations, Med. Phys. 32 (6), June 2005, pp. 1460-1468.

A second monitoring system was evaluated that used one of the chambers in the dual-chamber component referred to above as well as a Faraday cup to infer the beam current. The ratio of the two signals provided an analog that varied by a factor of 3.3 for beam energy variation from 6 MeV to 12 MeV, and $R_{80}$ varying from 20 mm to 40 m. This confirmed that the monitored features correlated to electron beam energy, and hence penetration depth with excellent signal sensitivity.

Figure 6:
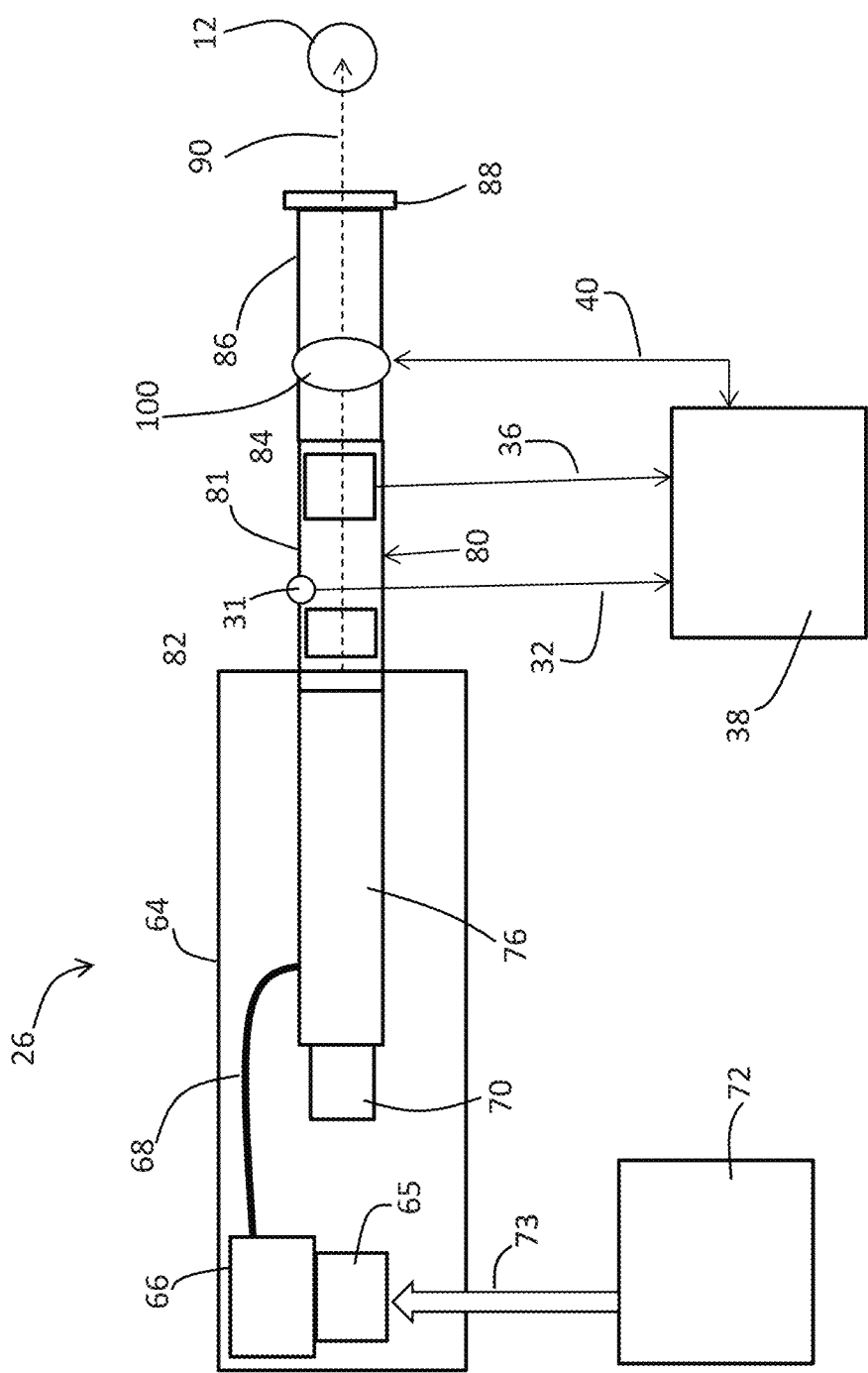
FIG. 6 schematically illustrates how feedback control can be implemented using absorber-based control.

FIGS. 6, 7, 8, 9A and 9B schematically illustrate how feedback control can be implemented by using control signals to adjust the setting of electron absorber components whose adjustment presents different degrees of absorption of the electron beam. FIG. 6 shows an embodiment of the electron beam generation unit 26 identical to unit 26 of FIG. 2, except that the applicator 86 of FIG. 6 is configured with features that allow operational mounting of an absorber 100 that can be adjusted to present stepwise or continuous adjustments to electron beam absorption and thereby tune the energy level of beam 16 via such tuning to desired settings. FIG. 6 shows how control system 28 directs control signal 40 to the absorber 100 for its controlled adjustment.

Figure 7:
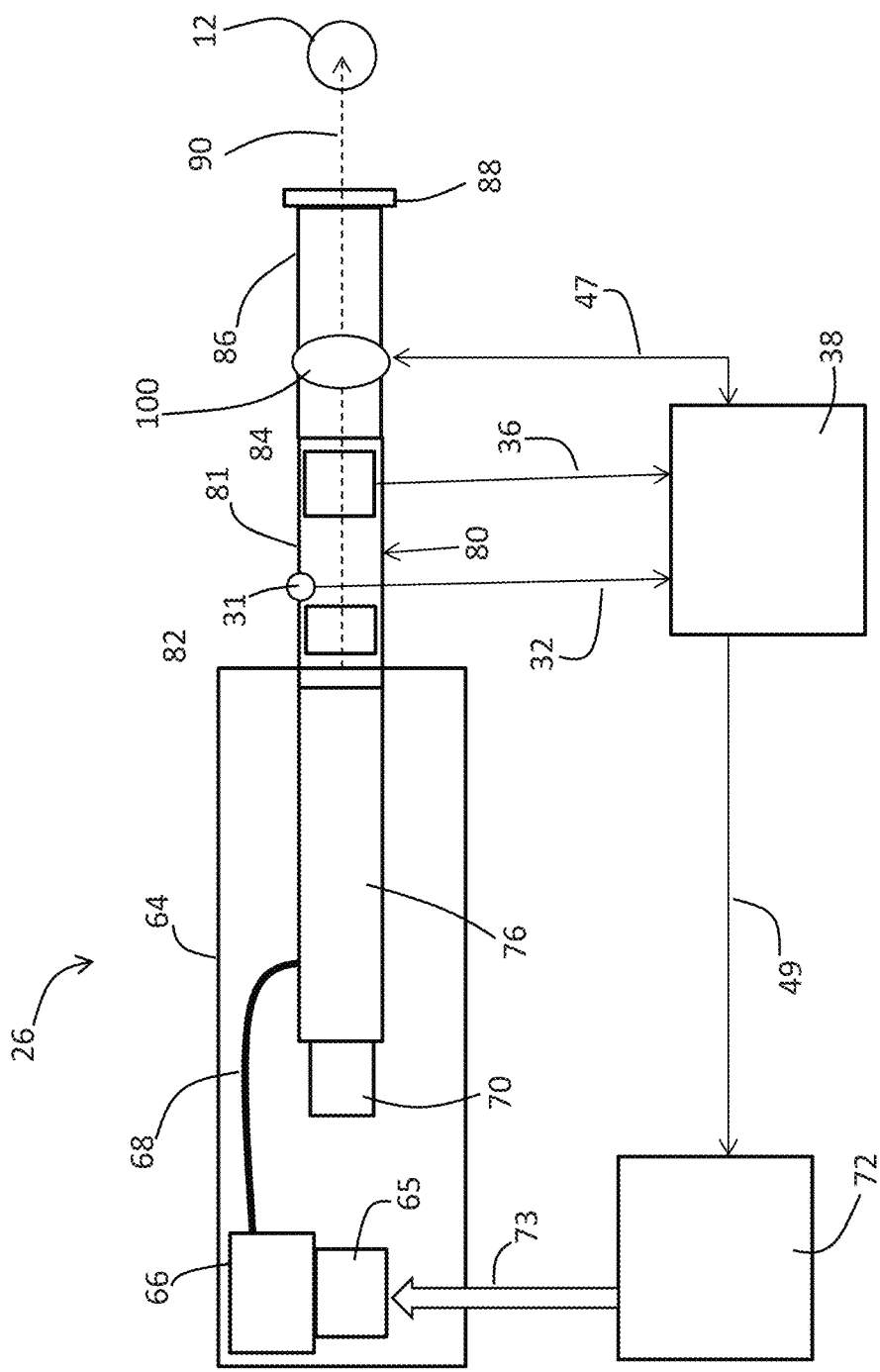
FIG. 7 schematically illustrates how feedback control can be implemented using both power-based and absorber-based control.

FIG. 7 schematically illustrates how feedback control can be implemented using both power-based and absorber-based control. FIG. 7 shows an embodiment of the electron beam generation unit 26 that is identical to unit 26 of FIG. 6, except that control system 28 of FIG. 7 sends a first control signal 47 to control the absorber 100 as well as a second control signal 49 to adjust power source(s) that generate the electron beam in order to electronically tune electron beam energy as desired. Using both kinds of control signals enhances the precision and ability to fine tune the energy of the electron beam 16 is continuous or extremely fine stepwise increments.

FIGS. 6 and 7 show how an absorber 100 can be integrated with applicator 86. Other deployments would be useful in other modes of practice in which the absorber is positioned in the path of the electron beam upstream from the target site. For example, the absorber 100 may beat the distal end of the applicator or at a mid-point of the applicator. In some embodiments, the absorber may be positioned above the target site between the applicator and the target site.

FIG. 8 schematically illustrates one embodiment of an absorber 100 useful for tuning electron beam energy. Absorber 100 is in the form of a tape or ribbon whose thickness in the path of electron beam 16 varies depending upon which segment 102, 104 or 106 is presented to the electron beam. Upon passage through a segment, electron beam 16 is tuned to a degree that correlates with the thickness of the segment. By providing an absorber with small incremental steps between segments, very small, stepwise adjustments to electron beam energy can be made. FIG. 8 shows absorber 100 as including three segments 102, 104 and 106 for purposes of illustration. In actual practice, absorber 100 preferably includes a greater number of steps to provide more tuning options. For example, absorber 100 may include at least 2 to 5, preferably 2 to 10, more preferably 2 to 20 segments that can be selectably presented to the electron beam for customized tuning at many different levels. As one suggested guideline, absorber 100 may include enough segments to correspond to 0.4 MeV to 1.0 MeV stepwise adjustments to the electron beam energy over a desired operating range.

In a preferred embodiment absorber 100 is in the form of a tape or ribbon of material comprising a plurality of segments of differing and graduated thickness. Each ribbon segment would have a thickness profile optimized for a particular depth of beam penetration and/or desired stepwise adjustment to electron beam energy. Desirably, each segment has a size to fill the applicator aperture. The tape could thread through opposing slits in the applicator 86 and be pulled through the applicator until the segment with the desired thickness and absorption profile is presented to the electron beam. Storage reels (not shown) may hold the end portions of the tape that are not presented to the electron beam. Motion of the reel(s) would position a tape segment having a different absorber thickness, and thus vary the corresponding depth-dose characteristic of the radiation delivered to the target site. Absorber 100 desirably has a density of at least 1 gm/cm$^3$ to facilitate electron beam absorption.

FIGS. 9A and 9B show an alternative embodiment of an absorber 120 useful for tuning electron beam energy. Absorber 120 is in the form of a rotatable disk having sectors 122 and 124 of different thicknesses. Absorber 120 rotates on axis 121 to present different sectors to the electron beam. The thickness of absorber 120 presented to electron beam 16 varies depending the rotational position of absorber 120 with respect to beam 16. Each sector 122 and 124 desirably fills the aperture of applicator 86 in those embodiments in which absorber 120 is integrated with applicator 86. Absorber 120 is shown as having two sectors 122 or 124. Other embodiments of absorber 120 may include 3 sectors, 4 sectors, or more.

In order to provide additional sector options for tuning electron beam 16, a rotatable absorber system comprising multiple rotatable disks (not shown), such as in a stack, may be used. For example, disks may have sectors that are open and do not obstruct or otherwise unduly impact penetration depth. In such a case, the degree of electron beam absorption can be tuned by rotating one or more sectors of one or more disks into the path of the electron beam. Thickness of the absorbing sectors can vary to allow tuning of the electron beam in relatively large or relatively small increments.

In some embodiments, an absorber may have a mesh-like or perforated configuration (not shown). Such a mesh structure would allow some fraction of the electrons in the beam to pass through unimpeded while still reducing the overall dose delivered to the target volume. The presentation of such a structure to the beam can be adjusted in order to tune the beam energy to a desired level.

Referring again to FIG. 1, system 10 optionally further includes at least one field defining shield 88. As shown, field defining shield is shown in a preferred deployment as being affixed to the exit or distal end of applicator 86. In other modes of practice, field defining shield 88 can be deployed in other locations. For example, field defining shield 88 can be deployed in a gap (if any) between the exit end of applicator 86 and the target site. Field defining shield 88 helps to define the field by functioning as a mask that selectively passes one or more desired portions of electron beam 16. For example, field defining shield 88 may be in the form of a plate having an aperture whose shape matches the desired target site, optionally with some extra margin of several millimeters to help ensure the full target site receives the irradiation dose. The electron beam is blocked by the solid portion of the plate, but is able to pass through the aperture to reach the target site. In exemplary embodiments, field defining shield 88 may include an aperture that helps to define a field at the target site that is up to as much as 10 cm in length and as much as 1 cm in width, but potentially as narrow as 0.4 cm. Non-contact treatment minimizes manipulation or disturbance of the target site.

Field defining shield 88 may be formed from one or more suitable materials. Field defining shield 88 may be fabricated from one or more materials. For example, in some embodiments, shield 88 is fabricated from 304 stainless steel which has been observed to provide an excellent combination of attenuation with low (<10%) backscatter, and is non-magnetic. Other stainless steels, such as 316 stainless steel or any 300 series stainless steel also would be suitable. In other modes of practice, field defining shield 88 comprises at least two different materials. These can be provided as a blend or as separate layers. Alternatively, the different materials may be provided as different components. A first material presented to the beam is a material with a lower atomic number (Z) to help reduce scattering of radiation. A second material presented to the beam is a dense material to absorb and block the electron beam. Thus, a field defining shield including both types of materials helps to adjust exposure pattern and the amount of scattered radiation that impinges on the patient through a combination of high density protectors (i.e. masks) to tune transmission to the patient, and low Z scatter shields, to absorb scattered radiation prior to reaching the patient. When used in contact mode, the high density protectors and/or low Z scatter shields may be flexible to conform to the shape of object being irradiated. An alternative embodiment of the field defining device would be placed on the patient or target volume and would be flexible to conform to the surface.

Materials suitable for higher absorption are dense, and typically are formed from materials including lead (Pb), tungsten (W), steel alloy, combinations of these, and the like. Such dense materials typically have a high electron density (often these are materials with high atomic number (Z)) and produce significant attenuation of radiation. They also may produce backscatter. Scattered dose to the target volume is undesirable. Generally scattered dose corresponds to lower energy electrons, and energy could be deposited at a shallower depth than desired for therapeutic effect. Accordingly, a less dense material in certain embodiments, a low Z mask is used to control Bremsstrahlung yield and scatter. Examples of lower Z materials that can help control electron scatter include polymethyl(meth)acrylate (PMMA), fused quartz, DELRIN polyoxymethylene, other polymers, copper, brass, combinations of these, and the like. One example of a field defining shield 88 comprises a thin layer of tungsten, a thicker layer of steel, and a layer of PMMA or fused quartz.

Generally, the size and weight of applicators and components such as field defining shield 88 could affect the patient and practitioner experience. Accordingly, using lighter weight materials or designs is better when lighter weight materials or designs are able to perform the desired function. An advantage at 2 MeV and below is that beams are readily attenuated in small amounts of material. Also, DELRIN (polyoxymethylene, or POM, commercially available from DuPont) can be used to form shields at such lower energy levels.

As another option when using system 10 of FIG. 1, flexible coverings (not shown) or the like can be draped over the patient to protect the patient from unwanted scatter. Such coverings may incorporate a dense material such as lead, for example. Additionally, protective screens, similar to those used in operating room fluoroscopy procedures, can be positioned around the patient during the treatment to protect the operator and other personnel from stray radiation exposure.

In certain embodiments, system 10 may be self-shielded and still be compact, relatively lightweight, and easy to deploy in many different ways. Self-shielded embodiments of system 10 of FIG. 1 do not require a radiation-shielded vault but rather may be deployed intraoperatively in an ordinary room, such as a surgical suite, an outpatient clinic office, emergency rooms, or in other areas that do not have additional radiation shielding. Personnel can remain in the treatment room thanks to the shielding incorporated into the apparatus design and the low energy of the scattered radiation. Conventional shields as used in fluoroscopy and in emergency rooms could serve to protect personnel. The invention may also be used outdoors and, if battery powered, may operate for a time without benefit of externally provided power.

Due to its compact and lightweight nature, system 10 may be mounted to a floor, wall, or ceiling. In some embodiments, system 10 may be mounted on a mobile stand so it can be easily moved from one location to another. For many procedures it may be desirable to be able to articulate system 10 in order to adjust treatment angle, treatment distance, and point of application, regardless of limitations on patient positioning, position, field size, and orientation. Accordingly, system 10 is lightweight and compact enough to be mounted on an articulating arm (not shown). The articulating arm may be configured to allow manual and/or motor control of system position and aim. For example, system 10 without applicator 86 may be moved into a desired position relative to a patient using motor control. Then, the applicator 86 can be attached and oriented by hand to the correct position.

FIGS. 10A and 10B show more details of embodiments of applicator 86 and field defining shield 88, wherein shield 88 is mounted to an end of applicator 86 closest to the target site (not shown in FIGS. 10A and 10B). Electron beam path 90 extends straight through applicator 86 and shield 88 and is aimed at the target site. Path 90 extends through open pathway 142 of applicator 86 to exit through slit 148 of shield 88. An interface coupling 140 is provided at the other end of applicator 86 to provide a docking interface with other components of unit 26 (see FIGS. 2 and 3). Length alignment rods 144 are used to help position applicator 86 and shield 88 a desired distance from the target site. One or more of these may be fitted to the end face of shield 88. Each set generally is of a uniform length for proper distance registration. Multiple sets of these may be provided to allow registration at a range of distances.

FIGS. 11A and 11B show applicator 86 and shield 88 of FIGS. 10A and 10B fitted with an endoscope mount 150. Mount 150 is attached to shield 88 using at least one mounting feature such as a screw that fits into bore 152. At least one male alignment and/or positioning feature 154 may be included in shield 88 and/or mount 150 to engage a complementary female feature on the other component. An endoscope (not shown) is inserted into aperture 156 Mount to view the target site.

The present invention will now be further described with reference to following the illustrative examples.

EXAMPLE 1

Figure 12:
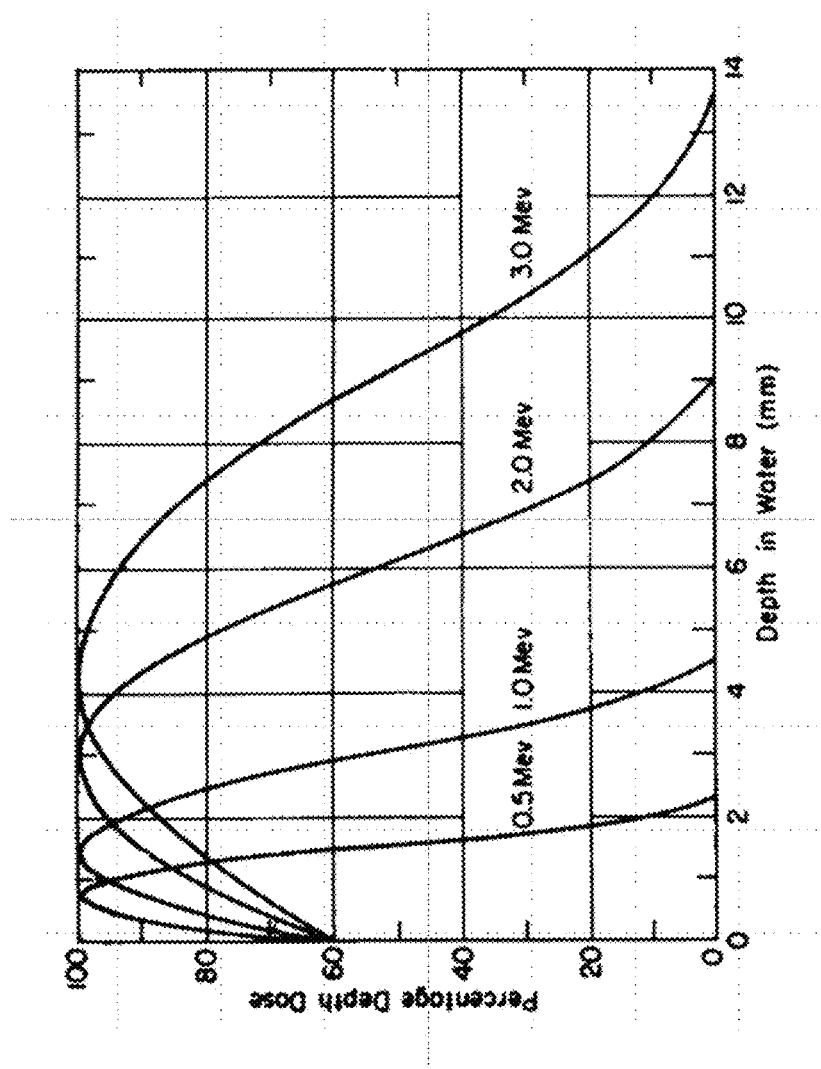
FIG. 12 shows plots of percentage depth dose versus depth in water for various low energy electron beams where the electrons were produced using a Van de Graaff machine.

FIG. 12 shows plots of percentage depth dose versus depth in water for various low energy electron beams where the electrons were produced using a Van de Graaff machine (from Gerald J. Hine and Gordon L. Brownell, Radiation Dosimetry, Academic Press, 1956).

The following Table 1 shows the corresponding $R_{80}$ penetration depths at different energy levels in water.

TABLE 1

| $R_{80}$ depth (millimeters) | Electron beam energy (MeV) |
|---|---|
| 1.3 | 0.5 |
| 2.5 | 1.0 |
| 4.8 | 2.0 |
| 7.4 | 3.0 |

Note that for electron radiation, the dose just below the surface increases to a maximum value and then falls sharply as the water attenuates the radiation. The data shows that penetration depth in a water phantom correlates strongly to energy level. For example, if the distal $R_{80}$ penetration depth is plotted against the energy using the data in Table 1, the resultant data is highly linear.

EXAMPLE 2

Effect of Field Flattening Device

Figure 13:
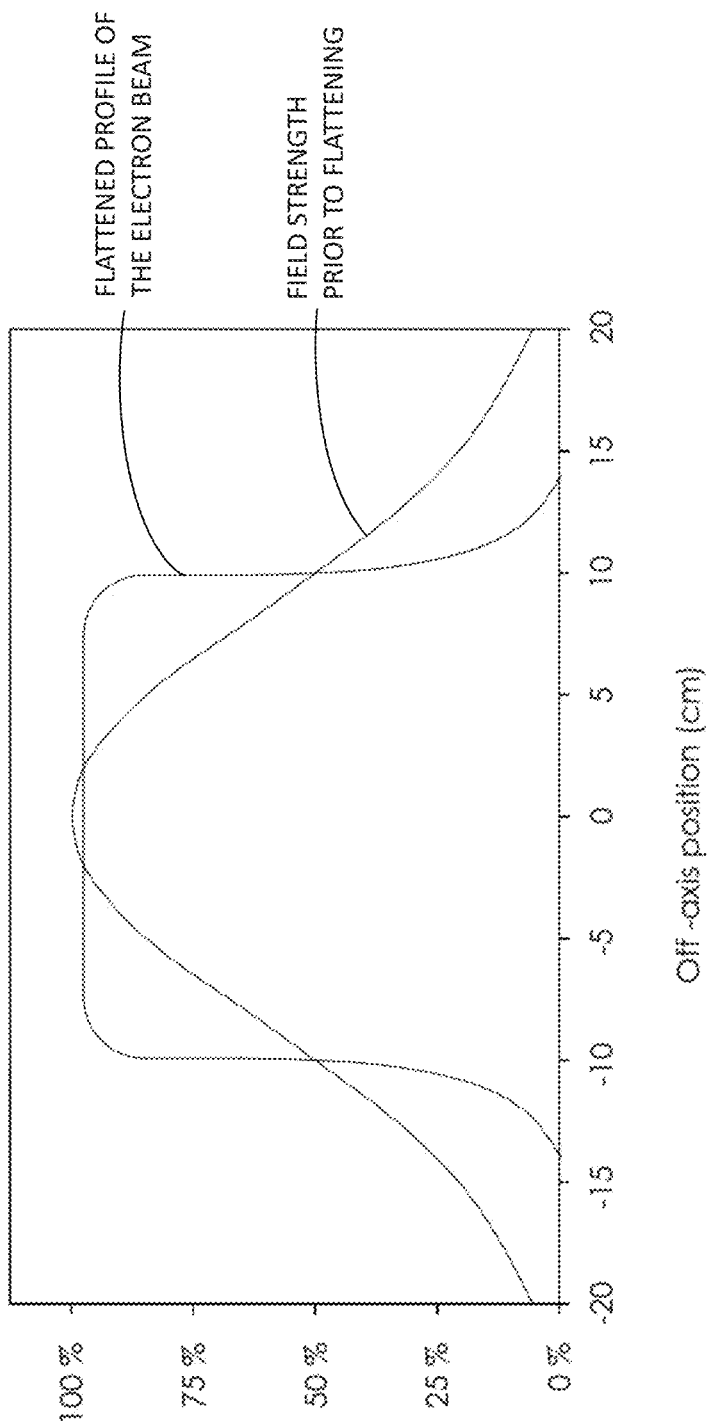
FIG. 13 illustrates the cross-beam profile of an electron beam before and after flattening

One purpose of scattering foils is to flatten and thereby provide an approximately uniform exposure of radiation to the target site. FIG. 13 illustrates the dose distribution measured perpendicularly to the beam axis. The peaked curve shows field strength prior to flattening. The other curve shows the flattened profile of the electron beam, which provides a more uniform dose distribution over a greater range of off axis positions.

EXAMPLE 3

Figure 14:
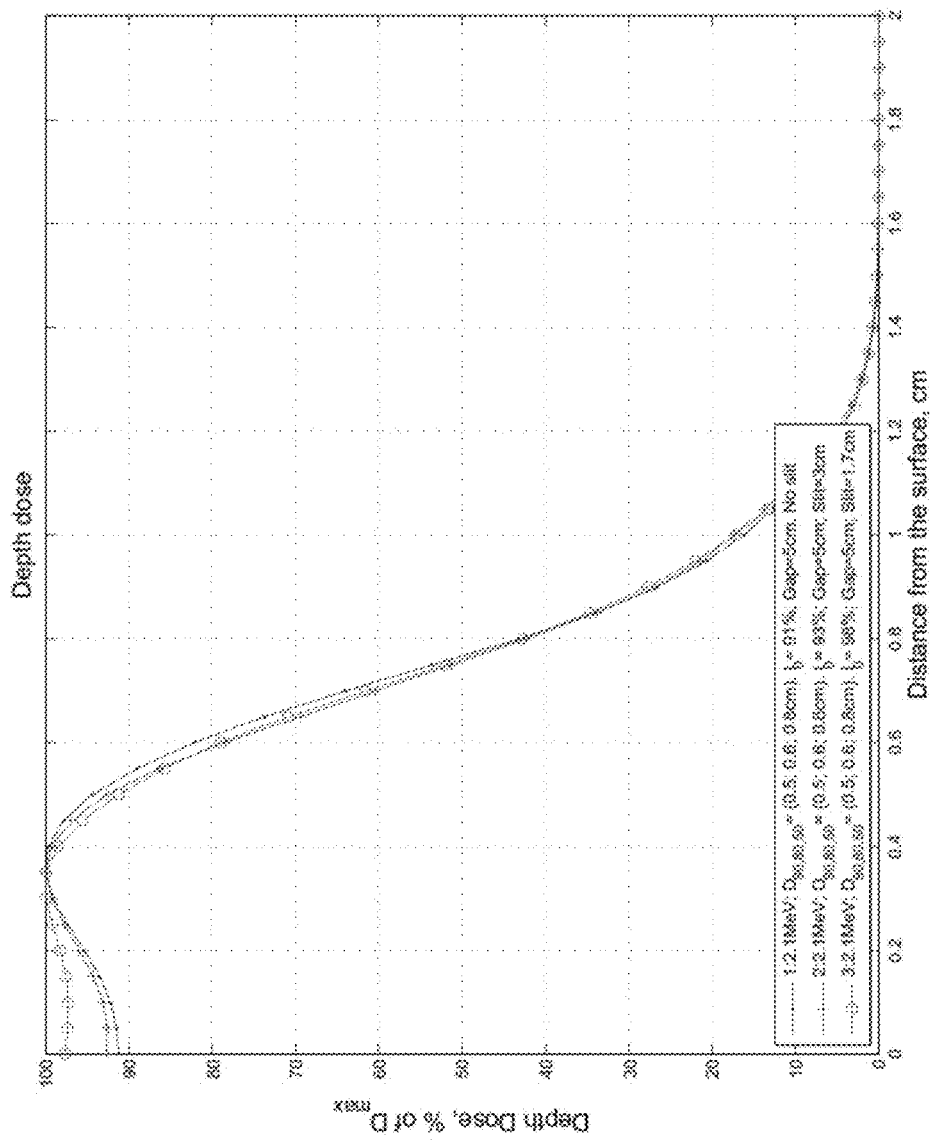
FIG. 14 shows percent depth dose as a function of penetration distance in water for 2.1 MeV electron beam system equipped with a 4.5 cm diameter applicator at a 5 cm distance (i.e. gap) from the target surface.

FIG. 14 shows percent depth dose as a function of penetration distance in water for 2.1 MeV electron beam system equipped with a 4.5 cm diameter applicator at a 5 cm distance (i.e. gap) from the target surface. Curves are shown for the open 4.5 cm applicator, a 4.5 cm applicator with a 3 cm slit, and a 4.5 cm applicator with a 1.7 cm slit. The slit material is fabricated from DELRIN polymer. For each curve, the surface dose ($I_o$) and the depth of the 90%, 80% and 50% doses are indicated. Note that a slit width less than 3 cm will elevate the surface dose. This data shows that there is a trade-off between slit width and surface dose. If it is desirable to reduce the surface dose, the slit width may need to be larger than the minimum width needed to cover the target.

EXAMPLE 4

Figure 15:
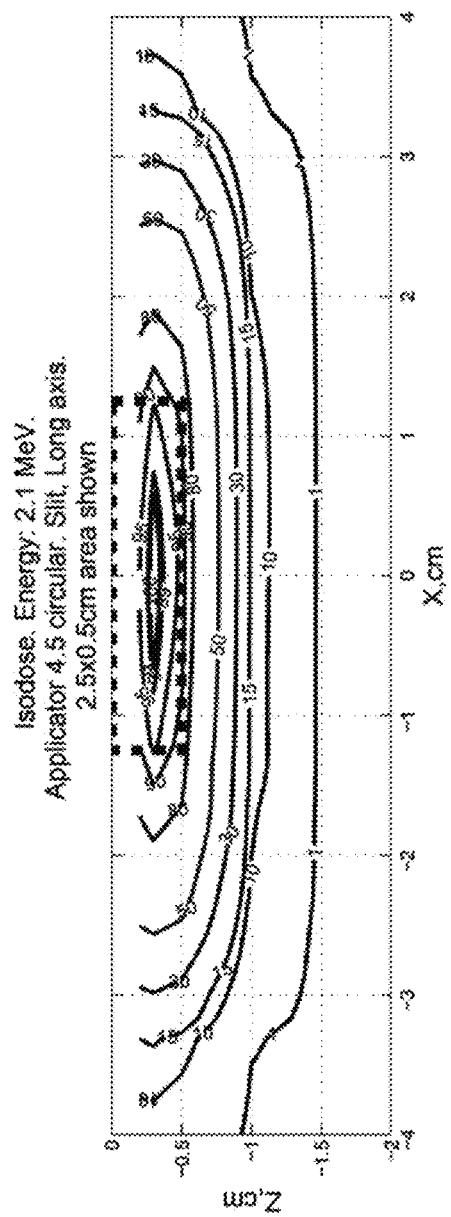
FIG. 15 shows an example of an isodose plot for electron beam radiation produced by a 2.1 MeV electron beam generator (MOBETRON machine, IntraOp Medical Corp., Sunnyvale, Calif.) equipped with a 4.5 cm applicator and a field defining shield fabricated from DELRIN polymer (referred to as polyoxymethylene, POM or polyacetal polymer commercially available from E.I. du Pont de Nemours and Company commonly known as DuPont) with a 3 cm wide× 4.5 cm long slit attached to the applicator treating with a 5 cm gap between the shield and the target site.

FIG. 15 shows an example of an isodose plot for electron beam radiation produced by a 2.1 MeV electron beam generator (MOBETRON machine. IntraOp Medical Corp., Sunnyvale, Calif.) equipped with a 4.5 cm applicator and a field defining shield fabricated from ORRIN polymer and having a 3 cm wide×4.5 cm long slit attached to the applicator treating with a 5 cm gap between the shield and the target site. The isodose plot is in a direction parallel to the slit opening, measured at the central axis of the slit opening. This shows that a field defining shield fitted to an applicator is effective to help define and limit the field of irradiation on the target site.

EXAMPLE 5

Figure 16:
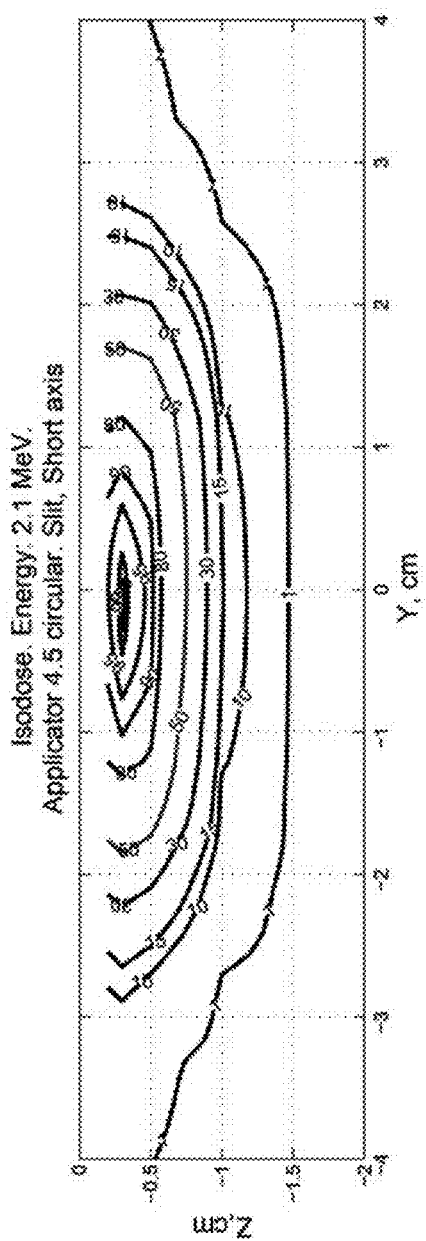
FIG. 16 shows an example of an isodose plot for electron beam radiation produced by a 2.1 MeV electron beam generator (MOBETRON machine, IntraOp Medical Corp., Sunnyvale, Calif.) equipped with a 4.5 cm applicator and a field defining shield (fabricated from DELRIN polymer) with a 3 cm wide×4.5 cm long slit attached to the applicator treating with a 5 cm gap between the shield and the target site.

FIG. 16 shows an example of an isodose plot for electron beam radiation produced by a 2.1 MeV electron beam generator (IntraOp Medical Corp., Sunnyvale, Calif.) equipped with a 4.5 cm applicator and a field defining shield fabricated from DELRIN polymer and having a 3 cm wide×4.5 cm long slit attached to the applicator treating with a 5 cm gap between the shield and the target site. The isodose plot is in a direction perpendicular to the slit opening, measured at the central axis of the slit opening. Comparing FIG. 16 to FIG. 15 shows how the 80% or 90% isodose lines are constricted by the presence of the shields. Note that if the slit were on the surface of the target or too close to the target, the surface dose would be increased.

EXAMPLE 6

Figure 17:
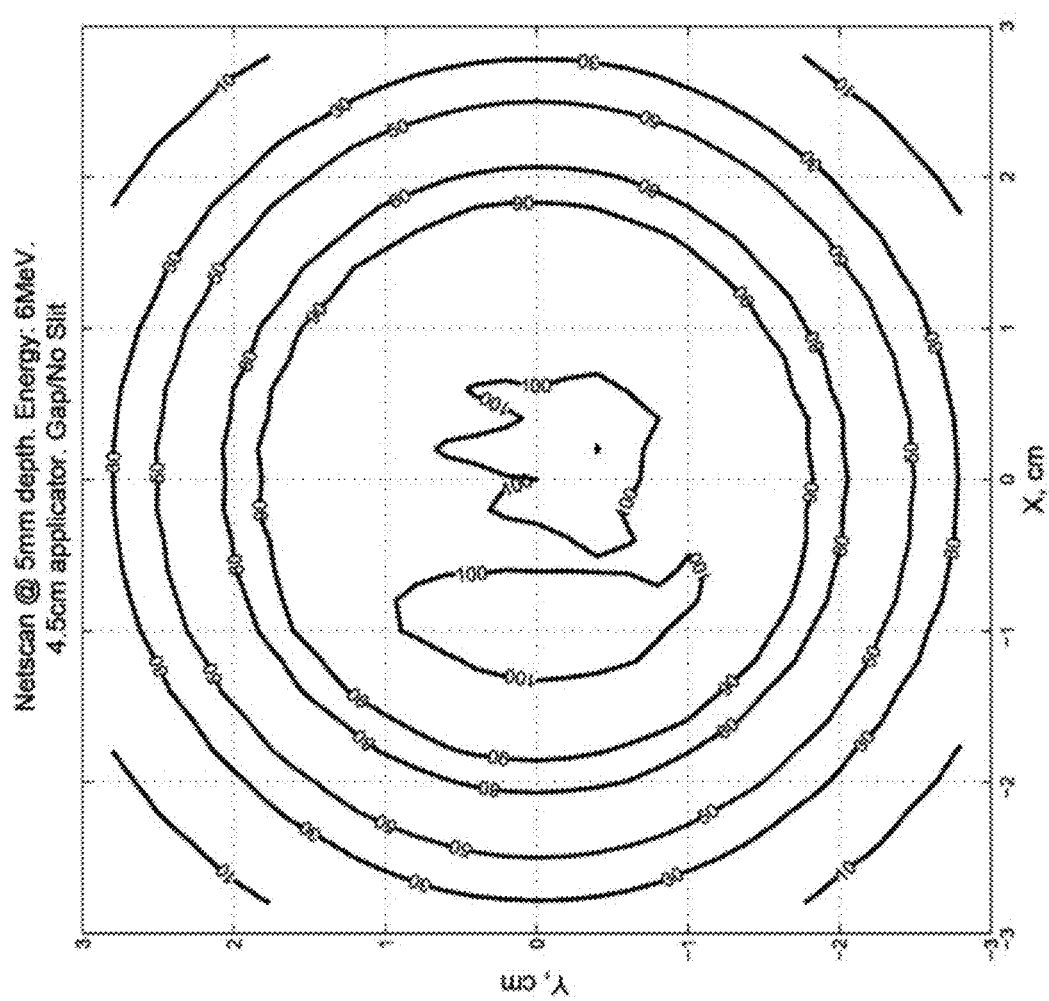
FIG. 17 shows an example of the dose distribution at a depth of 3 mm produced by a 2.1 MeV electron beam generator (MOBETRON machine, IntraOp Medical Corp., Sunnyvale, Calif.)) equipped with a 4.5 cm applicator and no slit installed.

FIG. 17 shows an example of the dose distribution at a depth of 3 mm produced by a 2.1 MeV electron beam generator (MOBETRON machine, IntraOp Medical Corp., Sunnyvale, Calif.)) equipped with a 4.5 cm applicator and no shield with a slit installed. Note that the dose distribution is symmetric in the plane of radiation with the 90% dose level extending in all directions about 1.8 cm from the center of the field.

EXAMPLE 7

Figure 18:
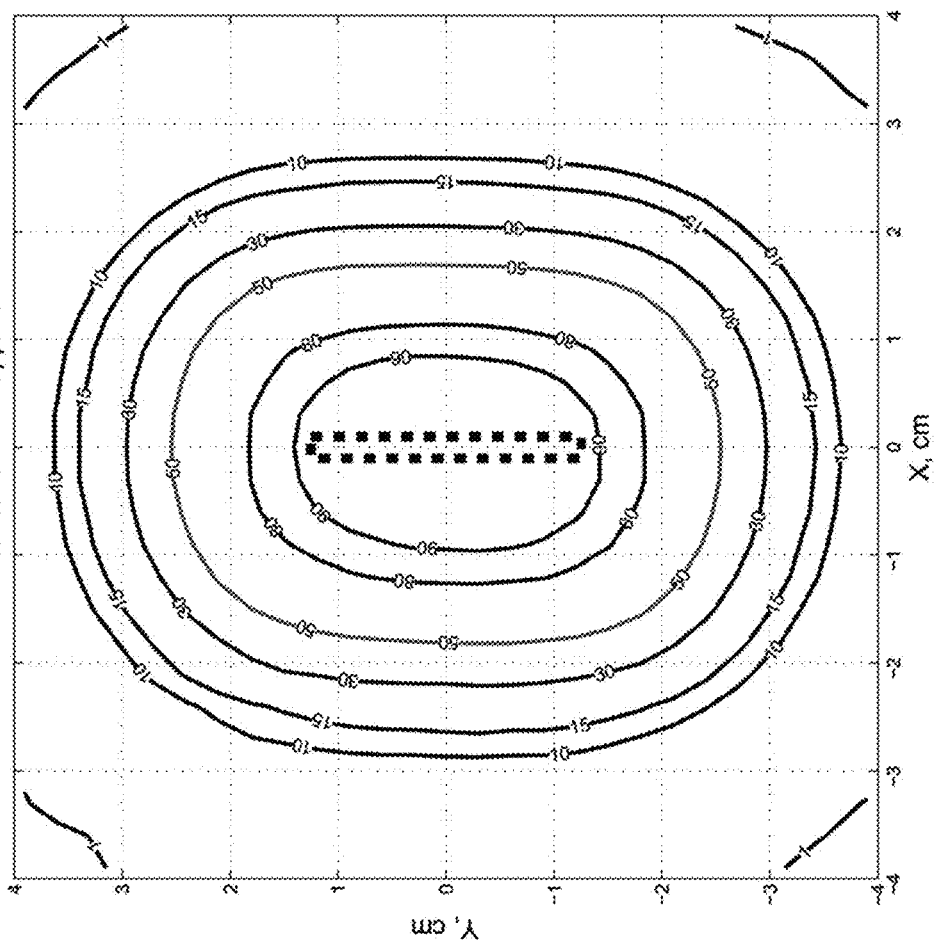
FIG. 18 shows an example of the dose distribution at a depth of 3 mm produced by a 2.1 MeV electron beam generator (MOBETRON machine, IntraOp Medical Corp., Sunnyvale, Calif.) equipped with a 4.5 cm applicator and a field defining shield (made from DELRIN polymer) with a 3 cm wide×4.5 cm long slit installed.

FIG. 18 shows an example of the dose distribution at a depth of 3 mm produced by a 2.1 MeV electron beam generator (MOBETRON machine, IntraOp Medical Corp., Sunnyvale, Calif.) equipped with a 4.5 cm applicator and a field defining shield fabricated from DELRIN polymer and having a 3 cm wide×4.5 cm long slit installed. Compared to the dose distribution in FIG. 17 (no slit), the 90% dose level is constricted in both the direction perpendicular to the slit and the direction along the slit, thus providing a considerable dose reduction to tissues outside but adjacent to the target region.

EXAMPLE 8

Hypothetical Evaluation of Narrow Beam Irradiation Pattern for Scar Treatment Using a 4.5 cm Applicator with a Field Defining Slit Radiation has been shown to mitigate scar formation when delivered post-surgically over a three-day period. While highly effective, it often has been logistically complex to radiate the wound repair immediately following the repair surgery. The objective of these experiments will test how radiation delivered at the time of wound repair compares to post-surgical fractionated radiation treatment.

Materials and Methods: A standard MOBETRON SN016 instrument (IntraOp Medical Corp., Sunnyvale, Calif.), detuned to operate at 2.1 MeV, is used to perform the experiment. The instrument is equipped with a circular 4.5 cm diameter applicator with a DRAIN shield with a 3 cm wide by 4.5 cm long slit mounted to the distal end of the applicator. If retrofit with a feedback control system of the present invention, the instrument could use electron beams of a large number of selectable, controllable, and adjustable lower energies to achieve a plurality of penetration depth settings in fine or continuous increments.

Results—Percent Depth Dose (PDD) Analysis: The PDD curves for several experimental setups are presented in FIG. 14. The experimental setups to be tested include using a 4.5 cm circular applicator (C4.5), and a 4.5 cm applicator with a varying slit spacing. As shown in FIG. 14, a gap of 3 cm would be optimal for this experiment as narrower gaps would increase the surface dose. Measurements are made with a 5 cm spacing between the bottom of the slit and the target surface. Plastic positioning rods at the end of the applicator, as shown in FIG. 14, are used to confirm and measure the distance from the bottom of the slit to the target surface.

Output Factors: Output factors for the 3 cm gap spacing is measured to be 34% of the output without the DELRIN shield.

EXAMPLE 9

Hypothetical Clinical Study Protocol

The test animals will be 42 kg Yorkshire pigs. Pigs are chosen as their skin and human skin have similar healing properties. Four animals participate.

Qualified surgeons will inflict twenty (20) 2.5 cm-long incisions on each animal, and then will repair the incisions. This makes a total of 80 incision repairs for the experiment. The incisions will be made according to the wound pattern in FIG. 19, wherein distances are shown in centimeters. This pattern ensures that there will be no radiation overlap among repairs. Note also that this arrangement covers the 2.5 cm repaired incision (showed by heavy dotted lines) with the 90% isosdose curve, rapidly dropping to lower values beyond the edge of the slit.

Four (4) of the incisions on each animal will receive no radiation and act as controls. Four of the incisions on each animal will receive 4 Gy per day for three (3) days, beginning the day after the surgery. These daily irradiated repairs represent the current post-surgical irradiation method used in scar amelioration. Four of the incisions on each animal will receive 6 Gy on the day of the surgery promptly after incision closure. Four of the incisions on each animal will receive 9 Gy on the day of the surgery promptly after incision closure. Four of the incisions on each animal will receive 12 Gy on the day of the surgery promptly after incision closure. These last groups of incision repaired irradiation will test how a single dose of radiation delivered at the time of surgery compares to the current standard of three (3) post-surgical irradiation treatment of 4 Gy per treatment.

During the first month, short term toxicity will be evaluated weekly, looking at infection and healing. In particular, differences between irradiated scars and the controls will be noted. The scars will also be quantitatively assessed using commercial DERMASCAN equipment (cyberDERM, Inc., Media, Pa.) to assess a variety of scar conditions such as Scar thickness, Scar length, Scar color and Scar tension. In addition, we will measure the skin pH, skin temperature, scar hydration, Trans Epidermal Water Loss, and Elasticity. Measurements will be taken every 30 days after repair irradiation, for a total of three (3) months.

At Day 90 after repair irradiation, animal tissues may be further evaluated with respect to the following:
  i) Histology (H&E, Collagen 1, Collagen 3, IL6, elastin)
  ii) Cellular damage (Tunnel assay for detecting DNA fragmentation
  iii) Gene expression analysis (Microarray)

The following is an approximate schedule for the experiment:
  a) Day 1: Perform daily QA to assure MOBETRON is operating at the correct energy and output. Radiation on for <3 minutes. Create 20 scars per animal and Treat 4 animals per treatment plan (FIG. 19). This will consume the entire day, though radiation will be on only sporadically, about 2-3 minutes per scar irradiated.

b) Day 2: Perform daily QA. Radiation on for <3 minutes. Treat 4 scars per animal per treatment plan. This will take ~30 minutes or less per animal.
c) Day 3: Perform daily QA. Radiation on for <3 minutes. Treat 4 scars per animal per treatment plan. This will take ~30 minutes or less per animal.
d) Day 4: Perform daily QA. Radiation on for <3 minutes. Treat 4 scars per animal per treatment plan. This will take ~30 minutes or less per animal.

The animals will be fed and maintained for 90 days after the radiation through day 96, at which time tissues will be collected for the further evaluation.

Irradiation will be performed using a 5 cm gap (like conventional skin treatment). Use of a direct connect mount allows the applicators to attach directly to the head of the MOBETRON unit. The source-to-skin distance (SSD) will be adjusted to 5 cm using plastic rods to measure the gap from the bottom of the applicator to the surface of the animal. The following table describes the measured dose with a 5 cm gap between the bottom of the slit and the target surface:

| Parameter | 3 cm wide slit × 4 cm long Delrin slit |
|---|---|
| Surface Dose | ~90% |
| Dmax | 3 mm |
| D80 | 6 mm |
| D50 | 8 mm |
| Width of 90% Isodose in Long Direction | 3.0 cm |
| Width of 90% Isodose in Short Direction | 2.2 cm |
| Width of 15% Isodose in Long Direction | 6.5 cm |
| Width of 15% Isodose in Short Direction | 5.4 cm |

Using these measurements, it is clear that the scar spacing shown in FIG. 19 is sufficient to assure no overlap of radiation from a neighboring scar while permitting the entire length of the 2.5 cm scar to be irradiated to the 80% dose level.

The examples described herein are provided for the purpose of illustration only, and are not intended to be limiting unless otherwise specified. Thus, the invention should in no way be construed as being limited to the examples described herein, but rather, should be construed to encompass any and all variations which become evident as a result of the teaching provided herein.

What is claimed is:

1. An electron beam radiation system useful to irradiate a target site on a patient with electron beam radiation dose having a controlled and adjustable penetration depth, said system comprising:
   a) an electron beam aimed at the treatment site, said electron beam having an adjustable and controllable electron beam energy adjusted to correspond to a desired penetration depth; and
   b) a control system configured to permit controlling the electron beam, wherein the control system comprises a feedback system, comprising:
      i) first and second sensors presented to the electron beam in a manner effective to detect first and second characteristics of the electron beam;
      ii) a controller that uses the first and second characteristics to derive an analog characteristic and that uses information comprising the analog characteristic, a correlation between the analog characteristic and the electron beam energy, and a reference value to derive an error signal, and wherein the controller generates a control signal from the error signal and causes the control signal to control the penetration depth of the electron beam in a manner effective to adjust the penetration depth in increments in the range from 0.3 to 2 mm.

2. The electron beam radiation system of claim 1, wherein the control system computes the analog characteristic using a function comprising a ratio of the first and second characteristics of the electron beam, said first and second characteristics of the electron beam being non-negligible.

3. The electron beam radiation system of claim 1, wherein the first characteristic is sensed by a sensor comprising a toroid and the second characteristic is sensed by an ion chamber, and wherein an analog characteristic is derived from information comprising the first and second sensed characteristics.

4. The electron beam radiation system of claim 1, wherein the analog characteristic is derived from an electron beam characteristic sensed by a first radiation detector and an electron beam characteristic sensed by a second radiation detector, wherein the first and second radiation detectors have different response curves to incident electron beam radiation.

5. The electron beam radiation system of claim 1, wherein the first and second sensors detect first and second characteristics of a linearly accelerated, and straight through electron beam.

6. A method for irradiating a surgical incision site made at a time of a surgery, comprising the step of using the electron beam radiation system of claim 1 to deliver an electron beam radiation dose at the surgical incision site intraoperatively or within a time period of less than 5 hours of the time of the surgery, wherein the electron beam delivered to the surgical incision site has an electron beam energy of 0.1 MeV to 6 MeV.

7. The method of claim 1, wherein the target site comprises a blood vessel.

8. The method of claim 1, wherein radiation occurs after anastomosis.

9. An electron beam radiation system useful to irradiate a target site on a patient with an electron beam radiation dose having a controlled and adjustable penetration depth, said system comprising:
   a) a power source providing a power output;
   b) a microwave source that receives the power output from the power source and emits microwave energy;
   c) a microwave network that receives the microwave energy from the microwave source;
   d) an electron beam source that emits an electron beam;
   e) an accelerator system configured to receive the electron beam from the electron beam source and to receive the microwave energy from the microwave network in a manner effective to accelerate the electron beam toward the target site;
   f) a collimator that receives and shapes the accelerated electron beam; and
   g) a feedback control system, comprising:
      1) a first electron beam sensor that measures a first characteristic of the accelerated electron beam;
      2) a second beam sensor that measures a second characteristic of the accelerated electron beam that is different from the first characteristic; and wherein:
      the feedback control system uses first and second signals from the first and second sensors to derive an analog characteristic of electron beam energy; and
      the feedback control system uses the analog of electron beam energy and a correlation between the analog of electron beam energy and the electron beam energy to generate a control signal that controls the electron beam energy at a level that is in the range from 0.1 MeV to 6 MeV, that adjusts the penetration depth in increments in the range from 0.3 mm to 2 mm, and that corresponds to a desired $R_{80}$ penetration depth at the target site.

10. An electron beam radiation system useful to irradiate a target site with electron beam radiation dose having an adjustable penetration depth, said system comprising:
   a) an electron beam directed at the target site, said electron beam having an adjustable and controllable electron beam energy adjusted to correspond to a desired penetration depth; and
   b) a library of electron beam absorbers configured to provide stepwise tuning of an electron beam in increments of 2 mm or less, wherein at least one electron beam absorber is presented to the electron beam in a manner to reduce the electron beam energy to control the penetration depth of the electron beam dose delivered to the target; and
   c) a feedback system configured to stabilize the penetration depth of a linearly accelerated, straight through electron beam having an electron beam energy, said system providing a control signal derived from a plurality of sensed electron beam characteristics that in combination correlate to the electron beam energy.

11. The electron beam radiation system of claim 10, wherein the absorber has a variable and selectable thickness, and wherein a selected thickness is presented to the electron beam in a manner to control the penetration depth of the electron beam delivered to the target.

12. The electron beam radiation system of claim 10, wherein system further comprises an applicator through which the electron beam is further shaped on an electron beam path directed at the target site, and wherein the absorber is coupled to the applicator.

13. A method for irradiating a target site on a patient with an electron beam radiation dose having a controlled and adjusted penetration depth, comprising the steps of:
   a) aiming an electron beam at the target site on the patient, wherein the electron beam has an adjustable and controllable electron beam energy adjusted to correspond to a desired penetration depth; and
   b) using a control system to adjust the electron beam to an energy effective to correspond to the desired penetration depth;
   c) using the control system to monitor the electron beam and to use at least first and second sensed characteristics to derive an analog of electron beam energy;
   d) using the control system to derive an error signal from information comprising the analog characteristic of the electron beam energy, a correlation between the analog characteristic and the electron beam energy, and a reference value; and
   e) using the control system to generate a control signal that controls the electron beam in a manner effective to adjust the penetration depth in increments in the range from 0.3 mm to 2 mm.

14. The method of claim 13, wherein the control system computes the analog characteristic using a function comprising a ratio of the first and second characteristics of the electron beam, said first and second characteristics of the electron beam being non-negligible.

15. The method of claim 13, wherein the first characteristic is sensed by a sensor comprising a toroid and the second characteristic is sensed by an ion chamber, and wherein an analog characteristic is derived from information comprising the first and second sensed characteristics.

16. The method of claim 13, wherein the analog characteristic is derived from an electron beam characteristic sensed by a first radiation detector and an electron beam characteristic sensed by a second radiation detector, wherein the first and second radiation detectors have different response curves to incident electron beam energy.

17. The method of claim 13, wherein first and second sensors detect the first and second characteristics of the electron beam after the electron beam is accelerated and flattened.

18. The method of claim 13, wherein first and second characteristics are first and second electron beam current values, wherein each current is sensed at a different location.

19. The method of claim 13, wherein the target site is irradiated intraoperatively.

20. The method of claim 13, wherein the target site comprises an incision.

21. The method of claim 13, wherein the target site comprises a tumor.

22. The method of claim 13, wherein the target site comprises a blood vessel.

* * * * *